United States Patent
Robitaille et al.

(10) Patent No.: US 10,314,991 B2
(45) Date of Patent: Jun. 11, 2019

(54) BREATHING APPARATUS AND METHOD FOR THE USE THEREOF

(71) Applicants: TRUDELL MEDICAL INTERNATIONAL, London (CA); Jean-Pierre Robitaille, London (CA)

(72) Inventors: Jean-Pierre Robitaille, Gaspe (CA); Stephen Costella, London (CA); Jennifer Pevler, London (CA); James Schmidt, London (CA)

(73) Assignee: TRUDELL MEDICAL INTERNATIONAL, London (CA)

(*) Notice: Subject to any disclaimer, the term of this patent is extended or adjusted under 35 U.S.C. 154(b) by 939 days.

(21) Appl. No.: 14/854,702

(22) Filed: Sep. 15, 2015

(65) Prior Publication Data

US 2016/0136372 A1 May 19, 2016

Related U.S. Application Data

(63) Continuation of application No. PCT/IB2014/000363, filed on Mar. 14, 2014.
(Continued)

(51) Int. Cl.
*A61M 16/00* (2006.01)
*A61M 16/20* (2006.01)
(Continued)

(52) U.S. Cl.
CPC ...... *A61M 16/0075* (2013.01); *A61M 16/006* (2014.02); *A61M 16/0072* (2013.01);
(Continued)

(58) Field of Classification Search
CPC .............. A61M 16/20; A61M 16/209; A61M 16/0006; A61M 16/0072; A61M 16/06;
(Continued)

(56) References Cited

U.S. PATENT DOCUMENTS

| 7,476 A | 7/1850 | Lane |
|---|---|---|
| 1,109,318 A | 9/1914 | Browne et al. |

(Continued)

FOREIGN PATENT DOCUMENTS

| EP | 274065 A1 | 7/1988 |
|---|---|---|
| EP | 1410821 A2 | 4/2004 |

(Continued)

OTHER PUBLICATIONS

Cleland et al., "Practical applications of Intravenous diuretic therapy in decompensated heart failure" Am J Med., 2006, 119 (12A): S26-S36.

(Continued)

*Primary Examiner* — Steven O Douglas

(74) *Attorney, Agent, or Firm* — Brinks Gilson & Lione

(57) ABSTRACT

A breathing assistance apparatus includes an inner volumetric member pressurizable from a first pressure to a second pressure and an outer volumetric member surrounding at least a portion of the inner expandable volumetric member. The inner volumetric member pressurizes the outer volumetric member as the inner volumetric member is pressurized from the first pressure to the second pressure. In another embodiment, a breathing assistance apparatus includes exhalation and inhalation chambers with respective biasing members providing for the exhalation chamber to apply a pressure to the inhalation chamber and thereby provide assisted inhalation. Methods for assisting breathing are also provided.

28 Claims, 33 Drawing Sheets

Related U.S. Application Data

(60) Provisional application No. 61/794,824, filed on Mar. 15, 2013.

(51) Int. Cl.
*A61M 16/06* (2006.01)
*A61M 16/08* (2006.01)
*A63B 23/18* (2006.01)
*A61M 16/10* (2006.01)
*A61M 16/04* (2006.01)

(52) U.S. Cl.
CPC ........ *A61M 16/0078* (2013.01); *A61M 16/06* (2013.01); *A61M 16/0875* (2013.01); *A61M 16/20* (2013.01); *A61M 16/208* (2013.01); *A61M 16/209* (2014.02); *A63B 23/18* (2013.01); *A61M 16/049* (2014.02); *A61M 16/0666* (2013.01); *A61M 16/0858* (2014.02); *A61M 16/0866* (2014.02); *A61M 16/107* (2014.02); *A61M 16/1045* (2013.01); *A61M 16/1055* (2013.01); *A61M 16/202* (2014.02); *A61M 2016/0027* (2013.01); *A61M 2202/0208* (2013.01); *A61M 2205/8206* (2013.01)

(58) Field of Classification Search
CPC .......... A61M 16/0666; A61M 16/0875; A61M 16/0075; A61M 16/0078; A61M 16/208; A61M 16/049; A61M 16/0858; A61M 16/0866; A61M 16/107; A61M 16/202; A61M 16/1045; A61M 16/1055; A61M 2016/0027; A61M 2202/0208; A61M 2205/8206; A63B 23/18
See application file for complete search history.

(56) References Cited

U.S. PATENT DOCUMENTS

| | | | |
|---|---|---|---|
| 2,711,170 A | 6/1955 | Bornstein | |
| 3,216,413 A | 11/1965 | Arecheta | |
| 3,537,488 A | 11/1970 | Liston | |
| 3,977,395 A | 8/1976 | Brawn | |
| 4,157,091 A | 6/1979 | Paupuch | |
| 4,320,754 A | 3/1982 | Watson et al. | |
| 4,323,078 A | 4/1982 | Heimlich | |
| 4,409,977 A | 10/1983 | Bisera | |
| 4,499,905 A | 2/1985 | Greenberg et al. | |
| 4,630,604 A | 12/1986 | Montesi | |
| 4,655,213 A | 4/1987 | Rapoport et al. | |
| 4,873,972 A | 10/1989 | Magidson et al. | |
| 4,879,996 A * | 11/1989 | Harwood, Jr. ........... A62B 7/10 128/202.26 |
| 4,934,360 A | 6/1990 | Heilbron et al. | |
| 4,967,742 A | 11/1990 | Theodorou | |
| 5,048,517 A | 9/1991 | Pasternack | |
| 5,052,384 A | 10/1991 | Kaneko | |
| 5,111,809 A | 5/1992 | Gamble et al. | |
| 5,284,160 A | 2/1994 | Dryden | |
| 5,649,533 A | 7/1997 | Oren | |
| 5,666,945 A | 9/1997 | Davenport | |
| 6,318,366 B1 | 11/2001 | Davenport | |
| 6,378,520 B1 | 4/2002 | Davenport | |
| 6,425,396 B1 | 7/2002 | Adriance | |
| 6,578,574 B1 | 6/2003 | Kohnke | |
| 6,595,212 B1 | 7/2003 | Arnott | |
| 6,629,529 B2 | 10/2003 | Arnott | |
| 6,763,828 B2 | 7/2004 | Arnott | |
| 7,007,693 B2 * | 3/2006 | Fuhrman ........... A61M 16/0096 128/204.22 |
| 7,284,554 B2 | 10/2007 | Shaw | |
| 7,487,778 B2 | 2/2009 | Freitag | |
| 7,533,670 B1 | 5/2009 | Freitag et al. | |
| 7,588,033 B2 | 9/2009 | Wondka | |
| 7,631,642 B2 | 12/2009 | Freitag et al. | |
| 8,302,603 B1 | 11/2012 | Weber | |
| 9,649,460 B2 * | 5/2017 | Robitaille ......... A61M 16/0075 |
| 9,987,447 B2 | 6/2018 | Robitaille et al. | |
| 2003/0150458 A1 | 8/2003 | Arnott | |
| 2003/0192543 A1 | 10/2003 | Arnott | |
| 2004/0074494 A1 | 4/2004 | Frater | |
| 2004/0094156 A1 | 5/2004 | Meakin | |
| 2004/0216741 A1 | 11/2004 | Arnott | |
| 2007/0295338 A1 | 12/2007 | Loomas et al. | |
| 2008/0115787 A1 | 5/2008 | Ingenito | |
| 2008/0167614 A1 | 7/2008 | Tolkowsky et al. | |
| 2010/0043796 A1 | 2/2010 | Meynink | |
| 2010/0132709 A1 | 6/2010 | Halpern | |
| 2011/0079224 A1 | 4/2011 | Arnott | |
| 2012/0234323 A1 | 9/2012 | Connor | |
| 2013/0118498 A1 | 5/2013 | Robitaille et al. | |
| 2013/0199531 A1 | 8/2013 | Ramanathan | |
| 2014/0311486 A1 | 10/2014 | Robitaille et al. | |
| 2015/0013676 A1 | 1/2015 | Dunlop | |
| 2017/0368278 A9 | 12/2017 | Robitaille et al. | |

FOREIGN PATENT DOCUMENTS

| | | | |
|---|---|---|---|
| EP | 1410821 B1 | 2/2008 | |
| EP | 1923089 A2 | 5/2008 | |
| GB | 1564273 A | 4/1980 | |
| JP | 4169936 B2 | 10/2008 | |
| WO | WO 2009/135294 A1 | 11/2009 | |
| WO | WO 2010/080709 A1 | 7/2010 | |
| WO | WO 2011/072220 A2 | 6/2011 | |
| WO | WO 2013/064888 A1 | 5/2013 | |

OTHER PUBLICATIONS

Collins et al., "The Use of noninvasive ventilation in emergency department patients with acute cardiogenic pulmonary edema: A systemic review" Ann Emerg Med., 2006, 48, pp. 260-269.

Hasselblad et al., "Relation between dose loop diurectics and outcomes in a heart failure population: Results of the ESCAPE trial" Eur J Heart Fail, 2007, 9, pp. 1064-1069.

Hubble et al., "Effectiveness of prehospital continuous positive airway pressure in the management of acute pulmonary edema" Prehosp Emerg Care, 2006, pp. 430-439.

International Search Report in International Application No. PCT/IB2014/000363 dated Jul. 14, 2014, 6 pages.

Levy et al., "Treatment of Severe decompensated heart failure with high-dose intravenous nitroglycerin; A feasibility and outcome analysis" Ann Emerg Med., 2007, 50, pp. 144-152.

Masip et al., "Noninvasive ventilation in acute cardiogenic pulmonary edema: Systematic Review and Meta-analysis" JAMA, 2005, 294, pp. 3124-3130.

Masip, "Noninvasive ventilation in acute cardiogenic pulmonary edema" Curr Opin Crit Care, 2008, pp. 531-535.

Mattu et al., "Prehospital management of congestive heart failure" Heart Fail Clin., 2009, pp. 19-24, v.

Mebazaa et al., "Practical Recommendations for prehospital and early in-hospital management of patients presenting with acute heart failure syndromes" Crit Care Med., 2008, 36[Suppl.]: S129-S139.

Taylor et al., "Prehospital noninvasive ventilation: A viable treatment option in the urban setting" Prehosp Emerg Care, 2008, 12, pp. 42-45.

Warner, "Evaluation of the effect of prehospital application of continuous positive airway pressure therapy in acute respiratory distress" Prehosp Disaster Med., 2010, 25, pp. 87-91.

Written Opinion of the International Searching Authority in International Application No. PCT/IB2014/000363 dated Jul. 14, 2014, 9 pages.

International Search Report and Written Opinion of the International Searching Authority for International Application No. PCT/IB2012/002230 dated Feb. 20, 2013, 10 pages.

Dodd, K.M., "What is Bipap/Cpap Therapy?," Ezine Articles,

(56) References Cited

OTHER PUBLICATIONS ezinearticles.com, submitted Jul. 28, 2007, obtained Oct. 20, 2010, 4 pages.

* cited by examiner

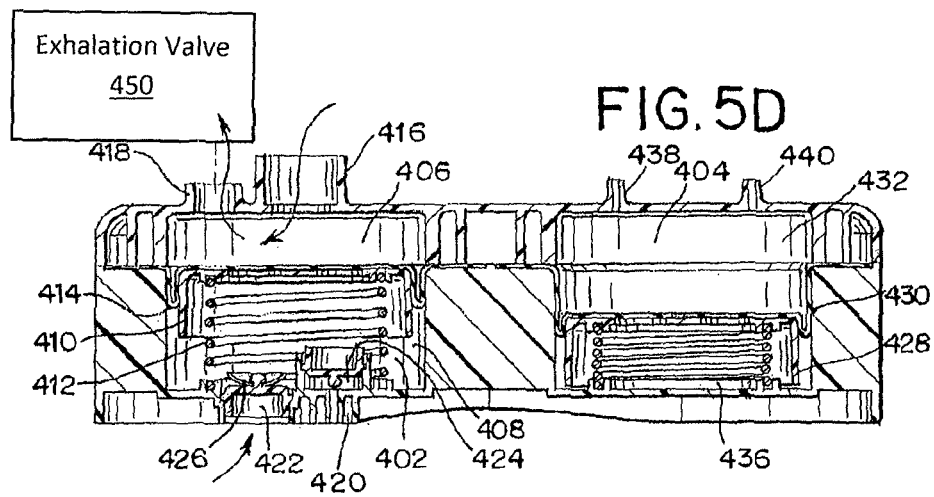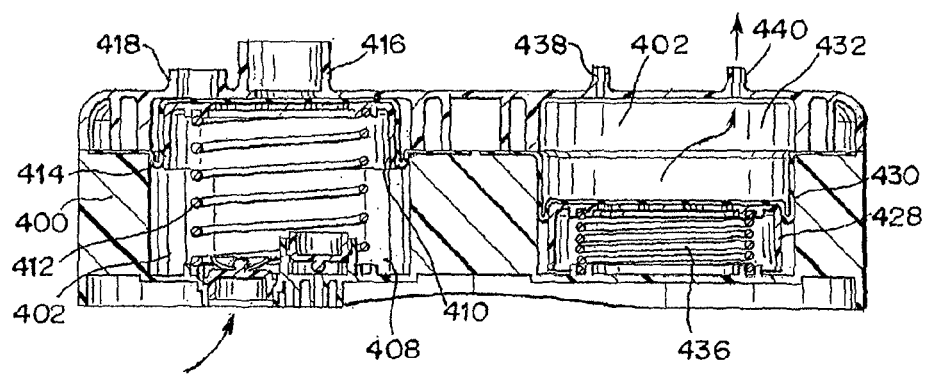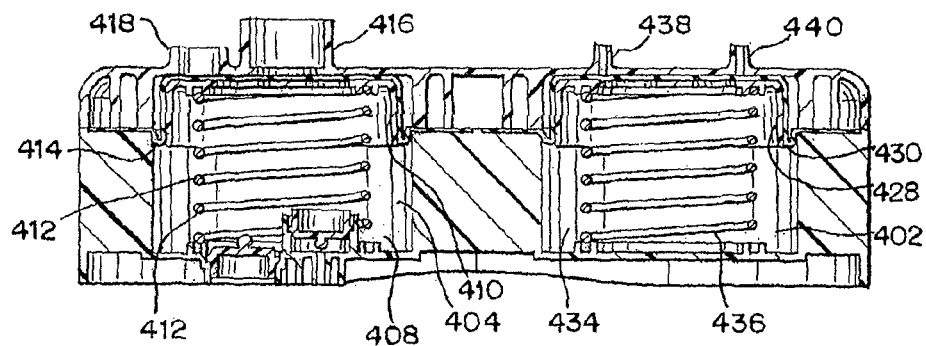

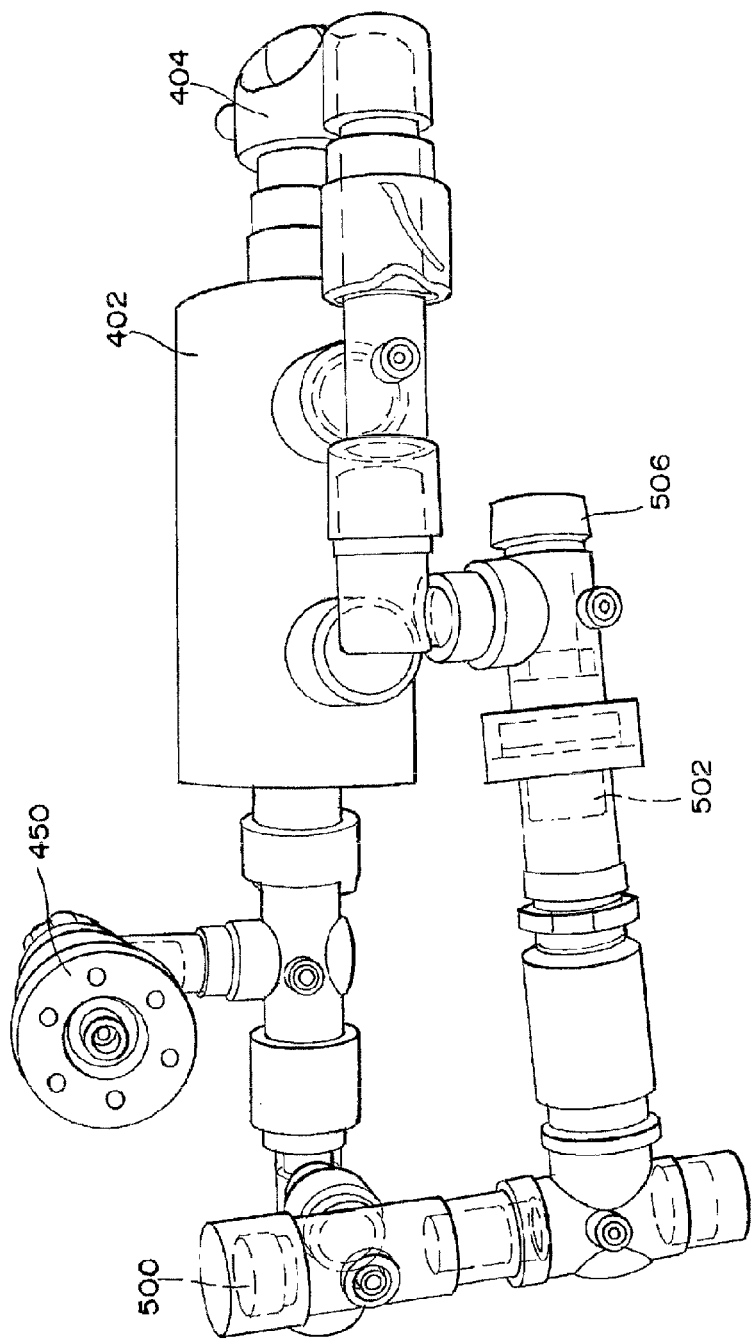

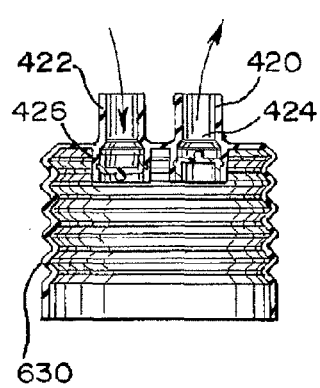
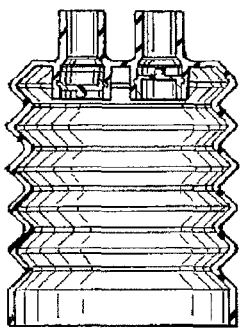
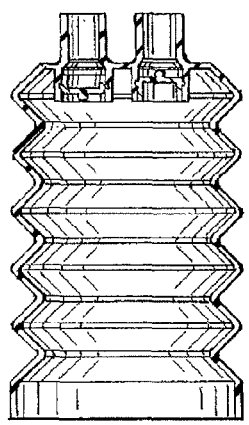
FIG.10A  FIG.10B  FIG.10C
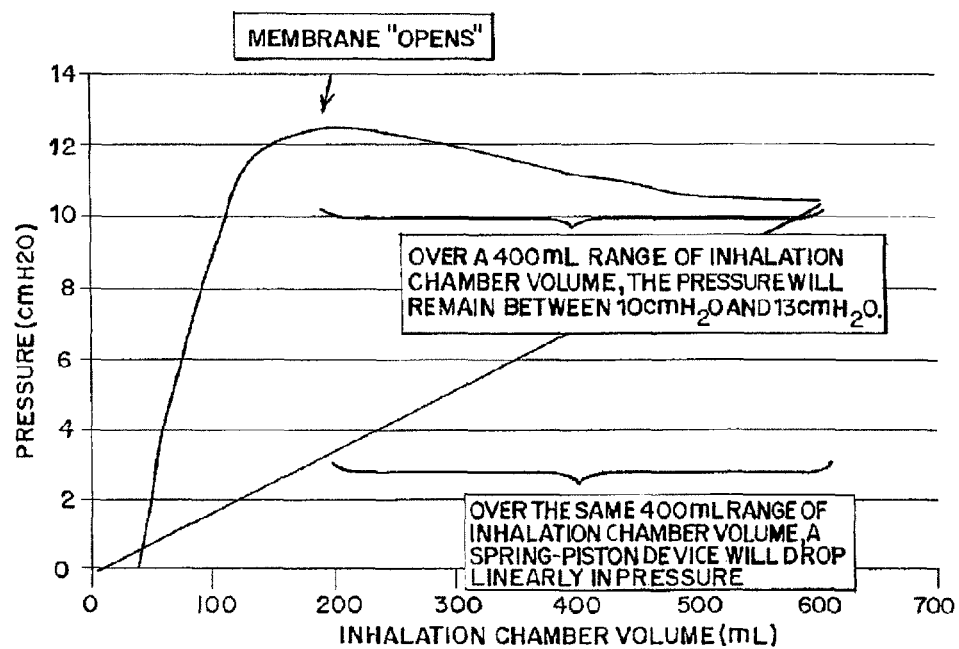
FIG.11

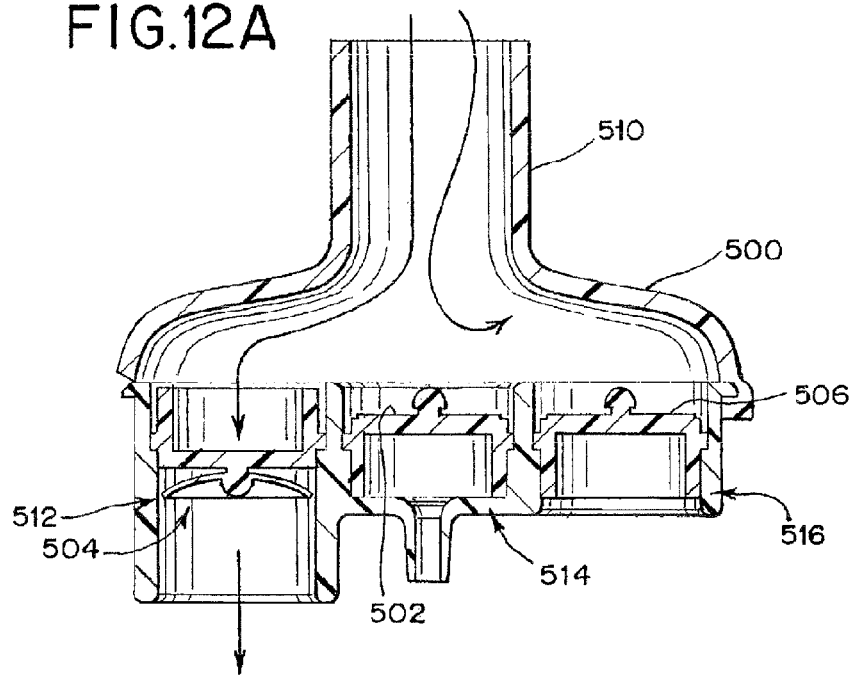
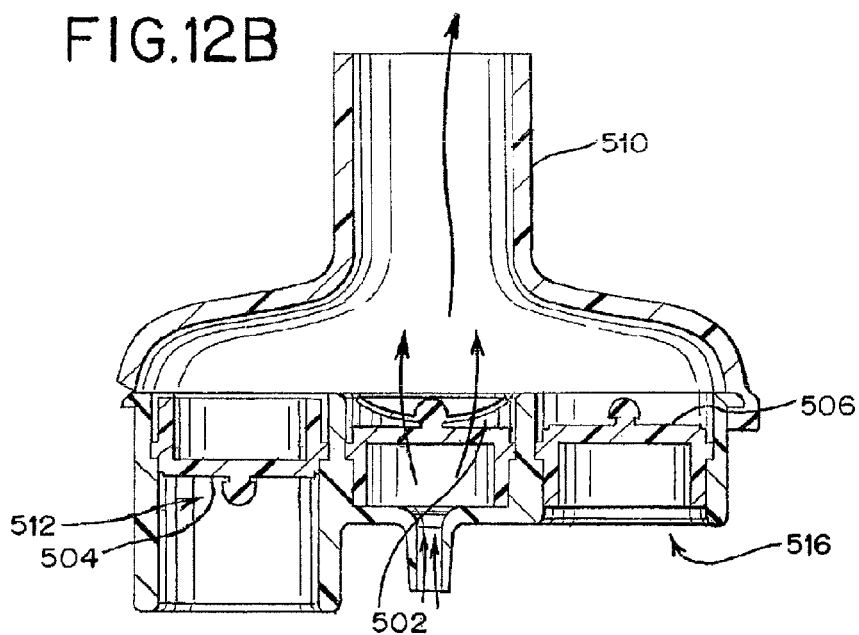

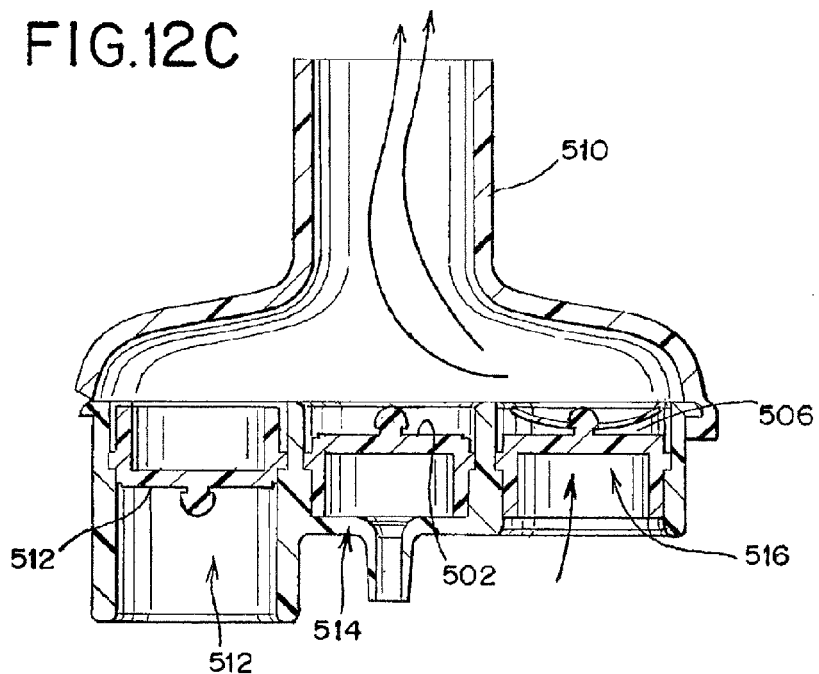
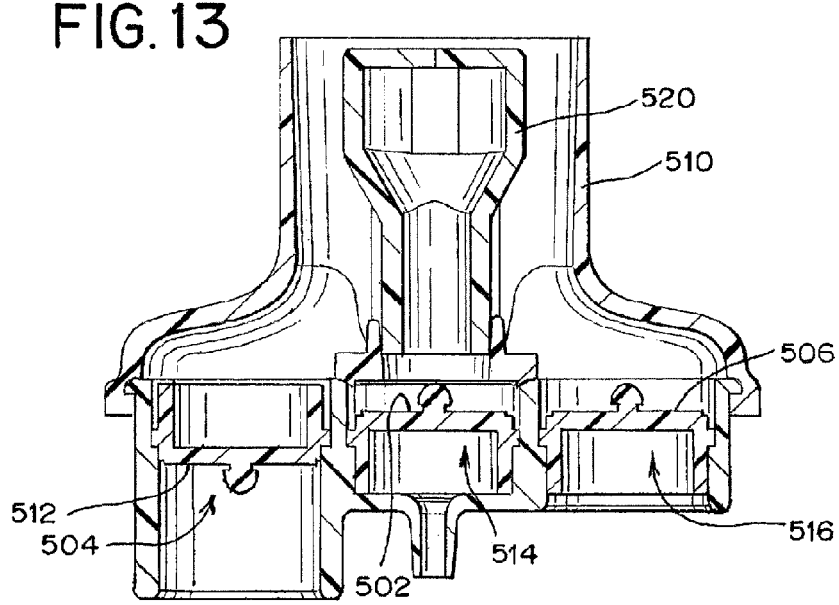

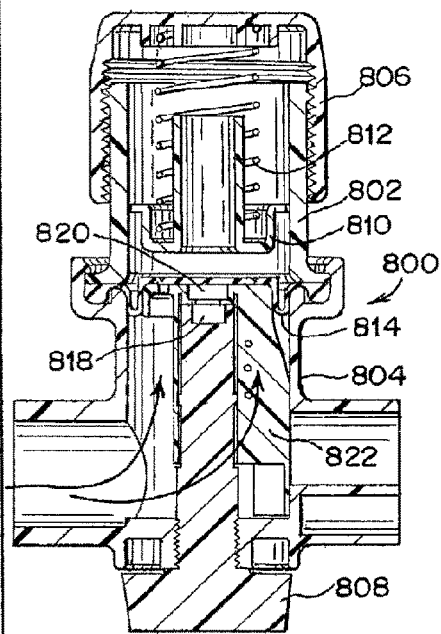
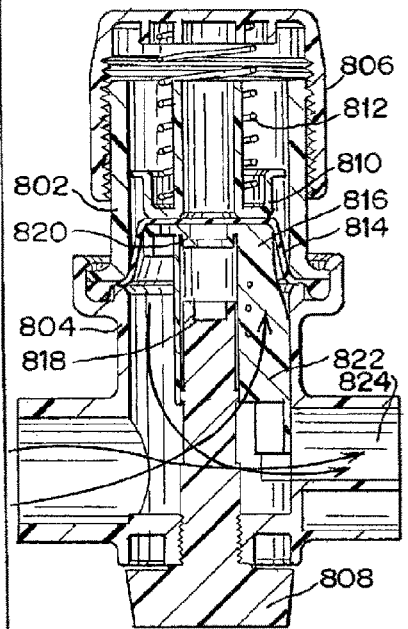
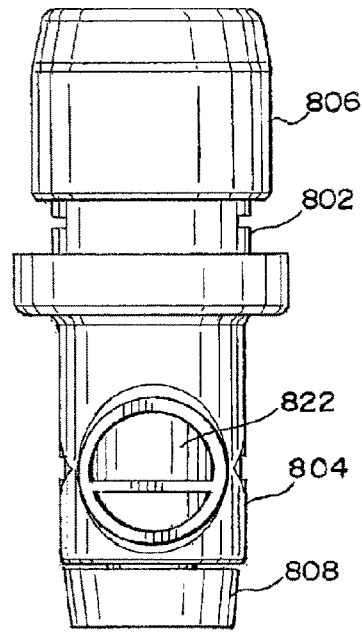
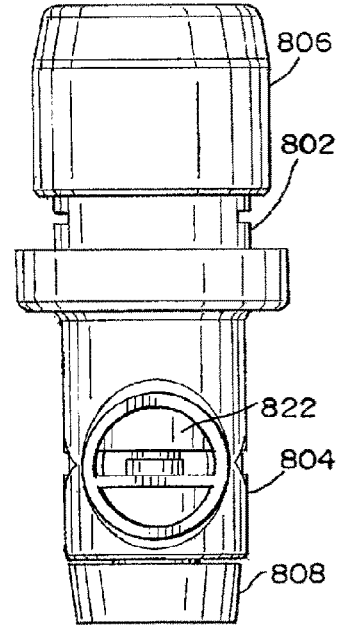

$F_i$: INTRINSIC DIAPHRAGM STIFFNESS
$F_p$: PRESSURE FORCE
$F_m$: ATTRACTIVE MAGNETIC FORCE $F_i$: INTRINSIC DIAPHRAGM STIFFNESS
$F_p$: PRESSURE FORCE
$F_s$: ATTRACTIVE MAGNETIC FORCE

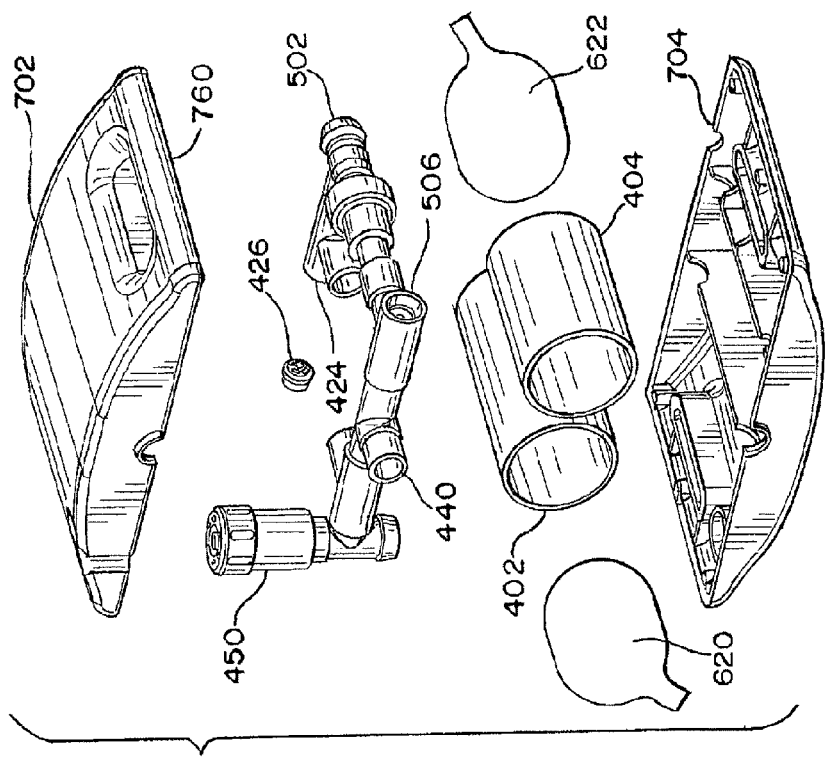
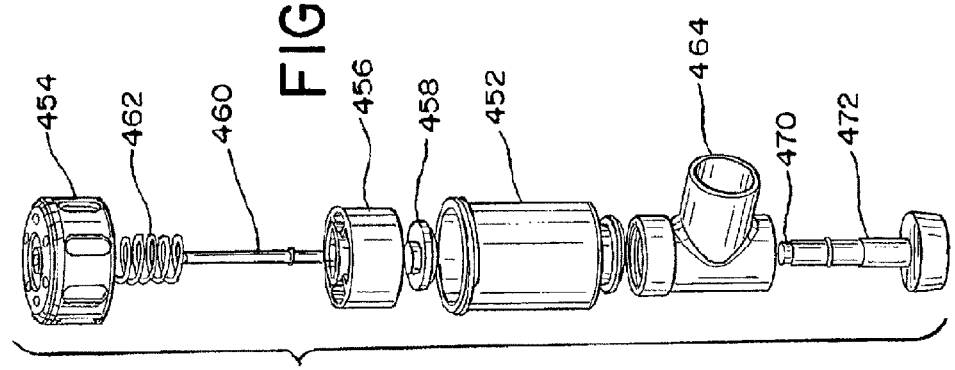

FIG. 25
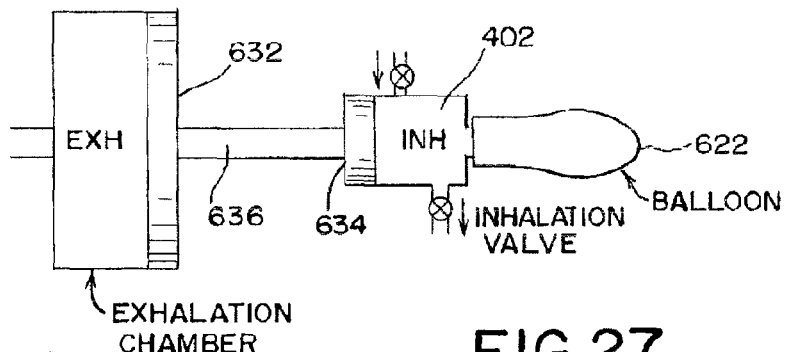
FIG. 26
FIG. 27
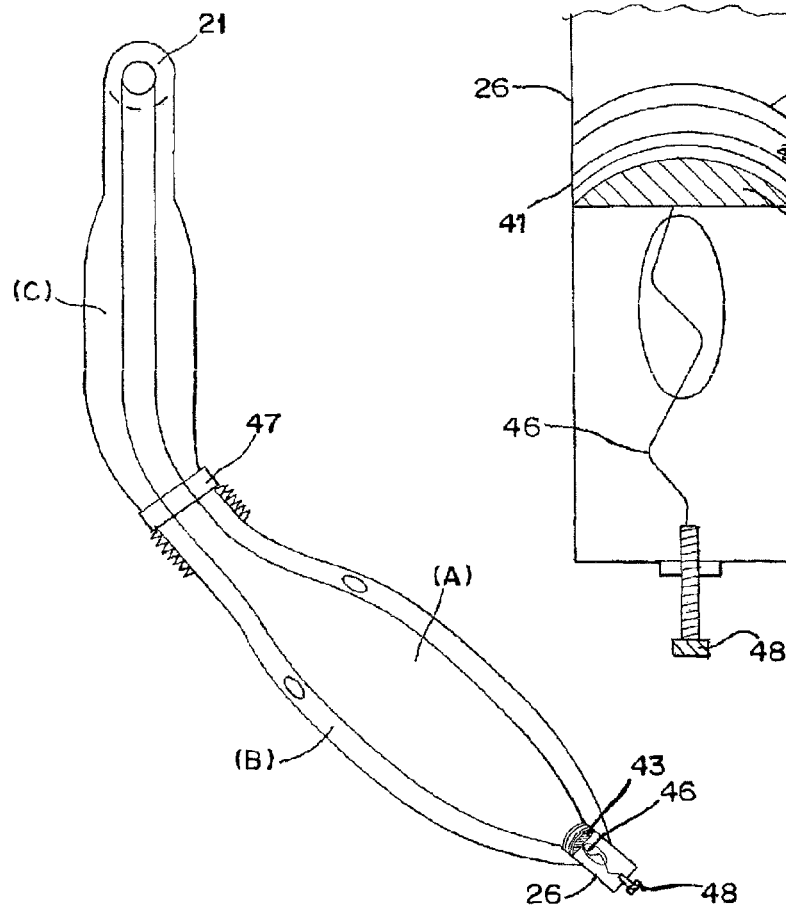

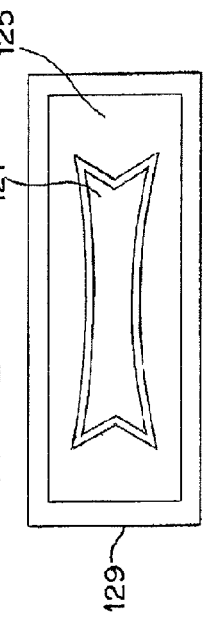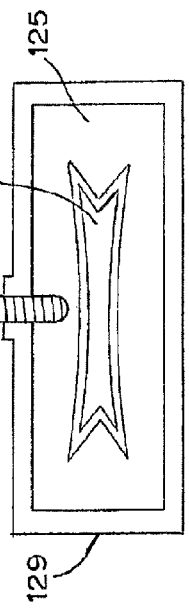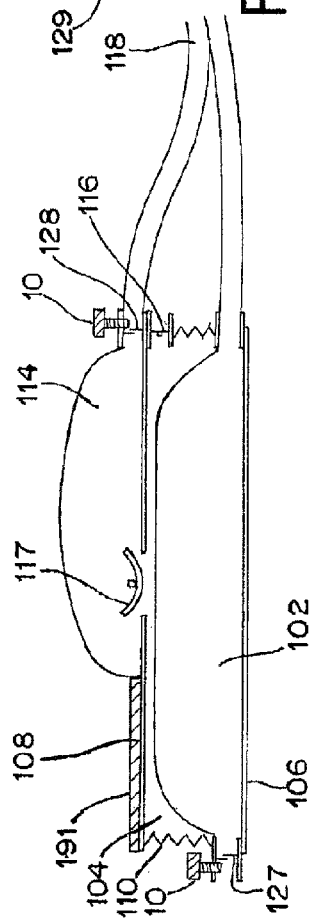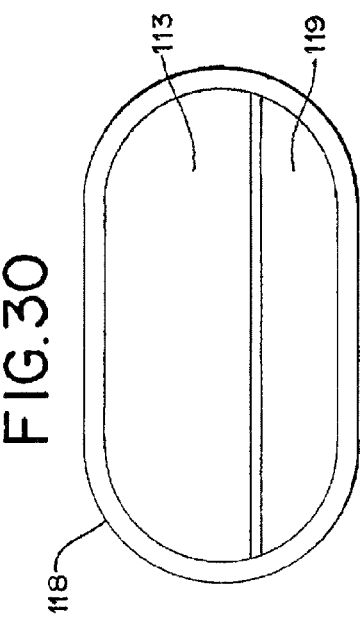

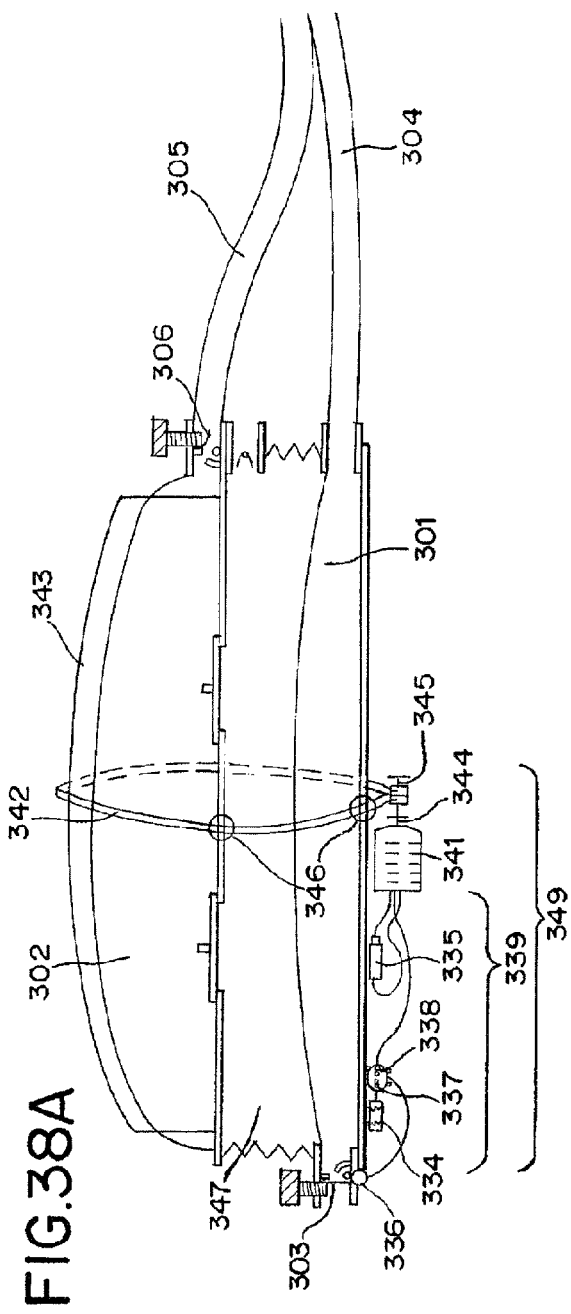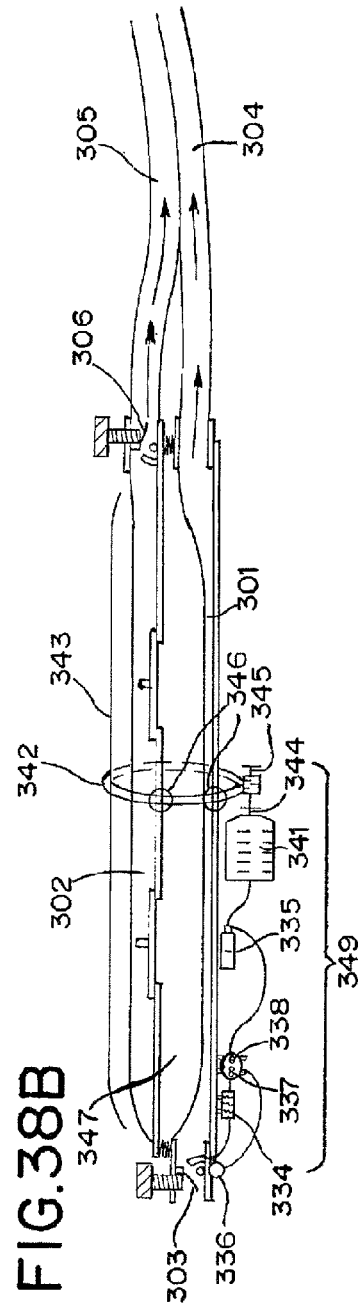

DURING THE FIRST TWO THIRDS OF EXHALATION

VALVE 127 OPENING

DURING THE LAST THIRD OF EXHALATION

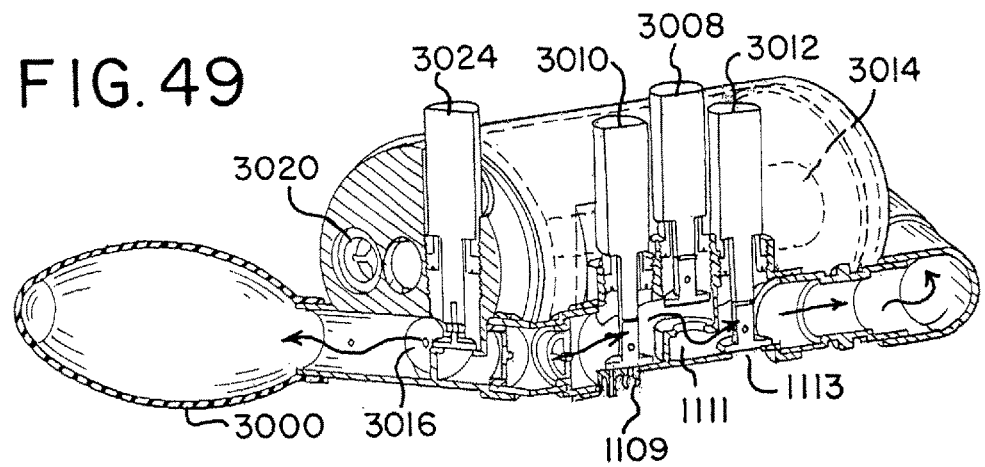
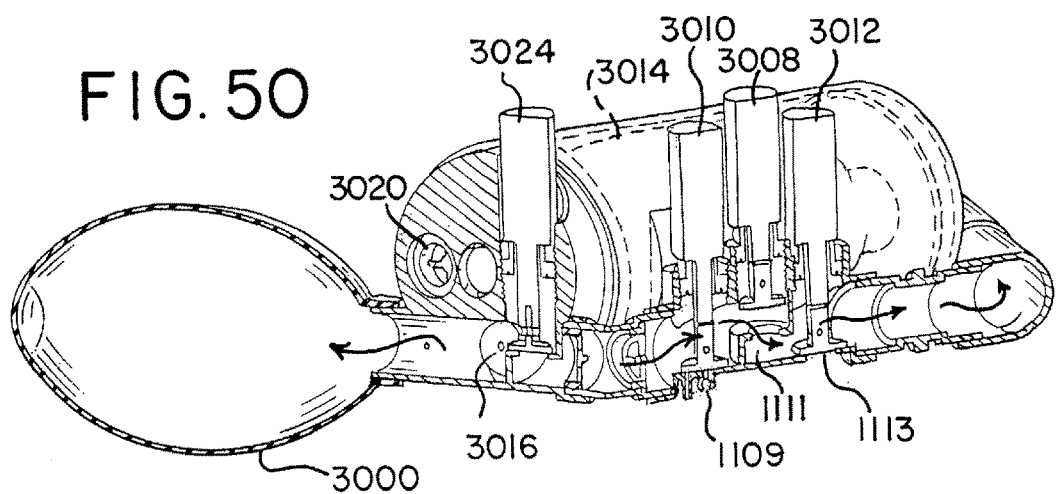
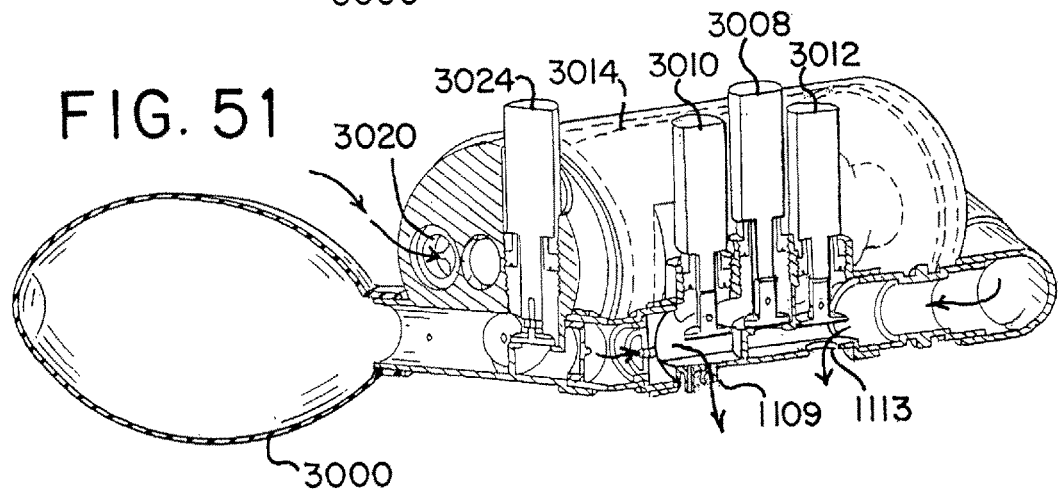

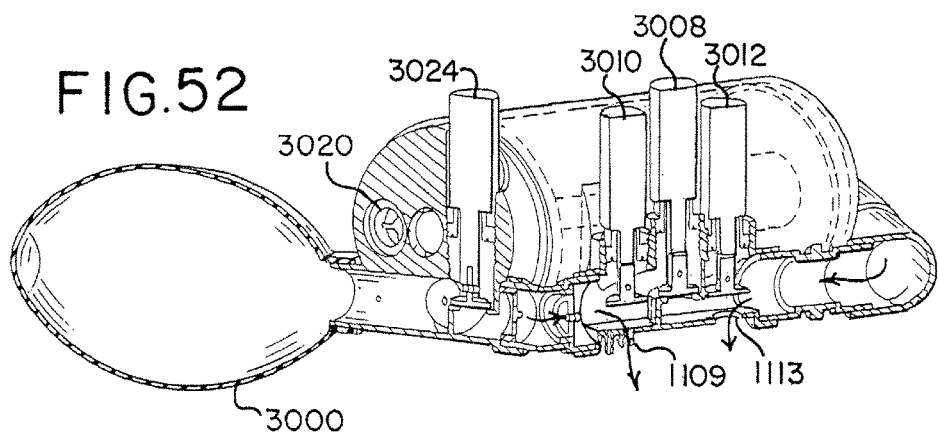
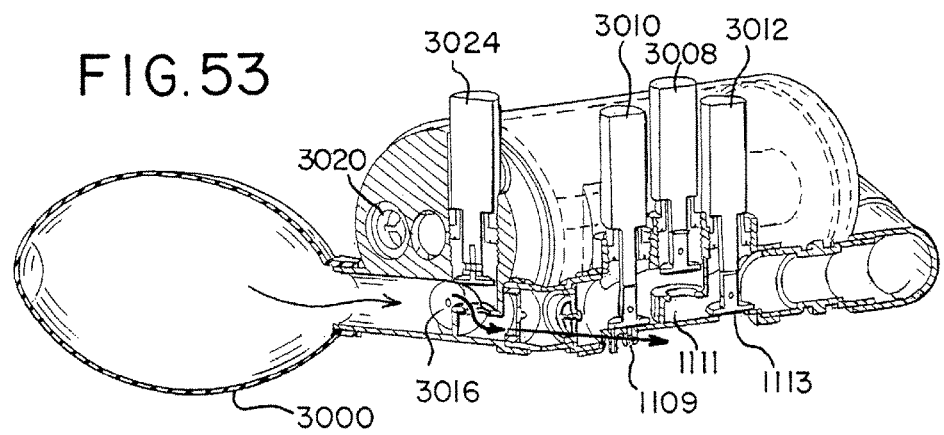

BREATHING APPARATUS AND METHOD FOR THE USE THEREOF

This application is a continuation of International Application No. PCT/IB2014/000363, filed Mar. 14, 2014, which claims the benefit of U.S. Provisional Application No. 61/794,824, filed Mar. 15, 2013, the entire disclosure of which is hereby incorporated herein by reference.

FIELD OF THE INVENTION

The present invention relates generally to an apparatus for administering respiratory therapy, including, without limitation, for assisting with breathing, reducing the work of breathing, performing breathing exercises and/or enhancing aerobic capacity, together with methods for the use thereof.

BACKGROUND

Many types of devices are available to administer respiratory therapy to a user, for example when the user is suffering from chronic obstructive pulmonary disease. Often, it may be desirable to apply a positive pressure during an inhalation sequence so as to assist the user when inhaling. At the same time, it may be desirable to provide positive expiratory pressure (PEP) during exhalation, for example to promote alveolar recruitment, reduce dynamic hyperinflation and prevent small airway and alveolar collapse. Typically, however, such benefits are achievable only through the use of expensive, non-portable equipment such as ventilators, bi-level positive airway pressure systems (BPAP) and/or continuous positive airway pressure systems (CPAPs). In addition, these types of devices typically use external pressure sources, for example supplemental oxygen and compressors, to provide pressure support, making them bulky and non-self sustaining.

SUMMARY

The present invention is defined by the claims, and nothing in this section should be considered to be a limitation on those claims.

In one aspect, a breathing apparatus includes an inner volumetric member pressurizable from a first pressure to a second pressure and an outer volumetric member surrounding at least a portion of the inner expandable volumetric member. The inner volumetric member pressurizes the outer volumetric member as the inner volumetric member is pressurized from the first pressure to the second pressure. An expiratory flow path communicates with the inner volumetric member. A one-way exhalation valve communicates with the inner volumetric member at a location spaced from the expiratory flow path. An inspiratory flow path communicates with the outer volumetric member, and an intake portal communicates with the outer volumetric member.

In another aspect, a breathing apparatus includes an exhalation chamber having a first biasing member dividing the chamber into first and second variable chambers. The first variable chamber includes an inlet port adapted for fluid communication with a user interface and an outlet port. The second variable chamber includes an inlet port and an outlet port. An inhalation chamber includes an inlet port in fluid communication with the outlet port of the second variable chamber, an outlet port in fluid communication with the user interface, and a second biasing member. The first biasing member is moveable from a first position to a second position in response to an exhaust flow from the inlet port of the first variable chamber, such that a volume of the first variable chamber is increased from a first volume to a second volume and a volume of the second variable chamber is decreased from a first volume to a second volume in response to the movement of said first biasing member. The second biasing member is moveable from a first position to a second position in response to a pressurized flow from the outlet port of the second variable chamber to the inlet port of the inhalation chamber. A volume of the inhalation chamber is increased from a first volume to a second volume in response to the movement of the second biasing member.

A method of assisting the breathing of a user includes exhaling through an expiratory flow path into an inner volumetric member, increasing a pressure of an exhaled gas inside the inner volumetric member, applying a pressure against an outer volumetric member with the inner volumetric member, releasing exhalation gases from the inner volumetric member, and inhaling through an inspiratory flow path from the outer volumetric member.

In another aspect, a method of assisting the breathing of a user includes exhaling an exhaled gas into an exhalation chamber divided by a first biasing member, applying a pressure to a first side of the first biasing member with the exhaled gas and moving the first biasing member in a first direction, applying a pressure with a second side of the first biasing member to an inhalable gas, applying a pressure to a first side of a second biasing member in an inhalation chamber with the inhalable gas, and inhaling the inhalable gas from the inhalation chamber while applying a pressure to the inhalable gas with the second biasing member.

The apparatus and method of use are configured to manually assist a user's breathing, in particular users who may suffer from chronic obstructive pulmonary disease. The apparatus provides some resistance to exhalation which is helpful in keeping the small airways open and in expanding the collapsed or partly collapsed alveoli. On inhalation, there is a build-up of pressure that takes place during a preceding exhalation maneuver, causing air trapped in a volumetric member to flow to the user, or patient. During inhalation, ambient air may be entrained into the flow path via inhalation ports. In this way, the apparatus assists breathing during inhalation by providing positive pressure, but also provides positive expiratory pressure during exhalation (PEP). The apparatus may also be used for manual inhalation assistance to assist with the work of breathing (inhalation/exhalation) or for manual ventilation. At the same time, the device may include one or more filters for removing impurities and microbes thereby improving air quality. Those filters may incorporate or be covered with substances that may be vaporized or sublimated. The device may also allow for warming or preheating of inhalation gases along with humidification of the inhalation gases.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

FIGS. 5A-F show the operations of another embodiment of a breathing assistance apparatus.

FIG. 9 is a plan view of the components incorporated in the breathing assistance apparatus shown in FIGS. 8A and B.

FIGS. 10A-C shown an adjustable exhalation chamber.

FIG. 11 is a graph comparing the inhalation pressure of one embodiment of the present device with a spring-piston device.

FIGS. 12A-C show the operation of one embodiment of a mouthpiece configured for the breathing assistance apparatus.

FIG. 13 shows an alternative embodiment of a mouthpiece.

FIGS. 15A-B show the operation of an alternative embodiment of a peak pressure and peep valve.

FIG. 23 is an exploded view of an alternative embodiment of a peak pressure and peep valve.

FIG. 24 is an exploded view of the breathing assistance apparatus shown in FIGS. 8A-9.

FIG. 25 is an alternative embodiment of a breathing assistance apparatus.

FIG. 26 is an alternative embodiment of a breathing assistance apparatus.

FIG. 27 shows a pressure relief valve arrangement used in the embodiment of FIG. 26.

FIGS. 28A-F and 29 are various schematic views of an alternative breathing assistance apparatus.

FIG. 30 is a cross section of an inspiratory and expiratory flow path tubing.

FIGS. 31A-C show an adjustable diaphragm valve.

FIGS. 38A and B show an embodiment of a breathing assistance device configured with the valve of FIG. 37.

FIGS. 49-54B show cross-sectional views of the device shown in FIG. 47 in various stages of operation.

DETAILED DESCRIPTION OF THE PRESENTLY PREFERRED EMBODIMENTS

It should be understood that the term "plurality," as used herein, means two or more. The term "longitudinal," as used herein means of or relating to length or the lengthwise direction. The term "lateral," as used herein, means situated on, directed toward or running from side to side. The term "coupled" means connected to or engaged with whether directly or indirectly, for example with an intervening member, and does not require the engagement to be fixed or permanent, although it may be fixed or permanent. The terms "first," "second," and so on, as used herein are not meant to be assigned to a particular component so designated, but rather are simply referring to such components in the numerical order as addressed, meaning that a component designated as "first" may later be a "second" such component, depending on the order in which it is referred. It should also be understood that designation of "first" and "second" does not necessarily mean that the two components or values so designated are different, meaning for example a first valve may be the same as a second valve, with each simply being applicable to different components, and that a first valve may later be referred to as a second valve depending on the order of reference, and vice versa. The term "upstream" refers to a direction opposite the direction of a flow, while the term "downstream" refers to a direction of a flow. Therefore, and for example, a fluid flows downstream from an upstream location to a downstream location.

Figure 1:
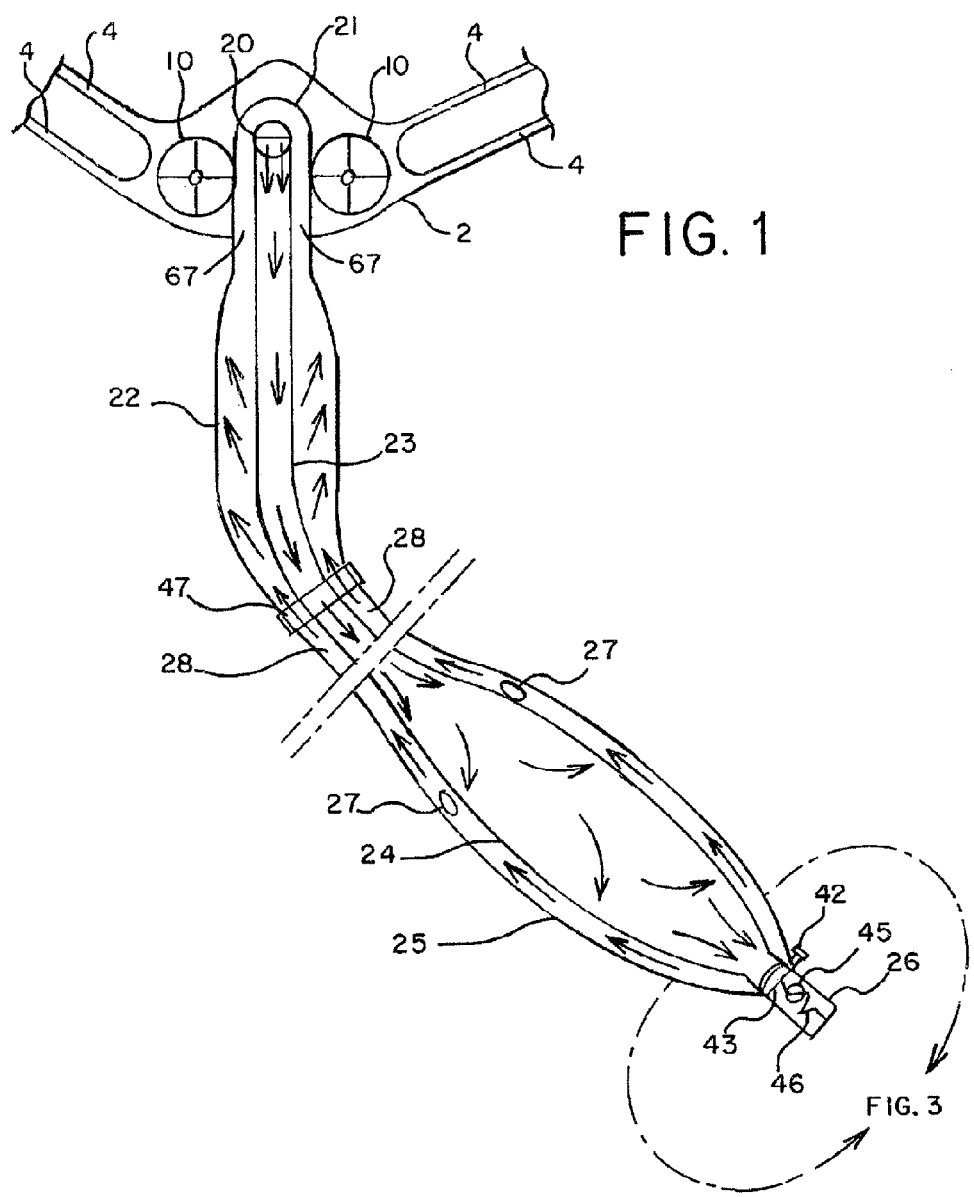
FIG. 1 is a schematic cross-sectional view of the breathing assistance apparatus during an exhalation sequence.
Figure 2:
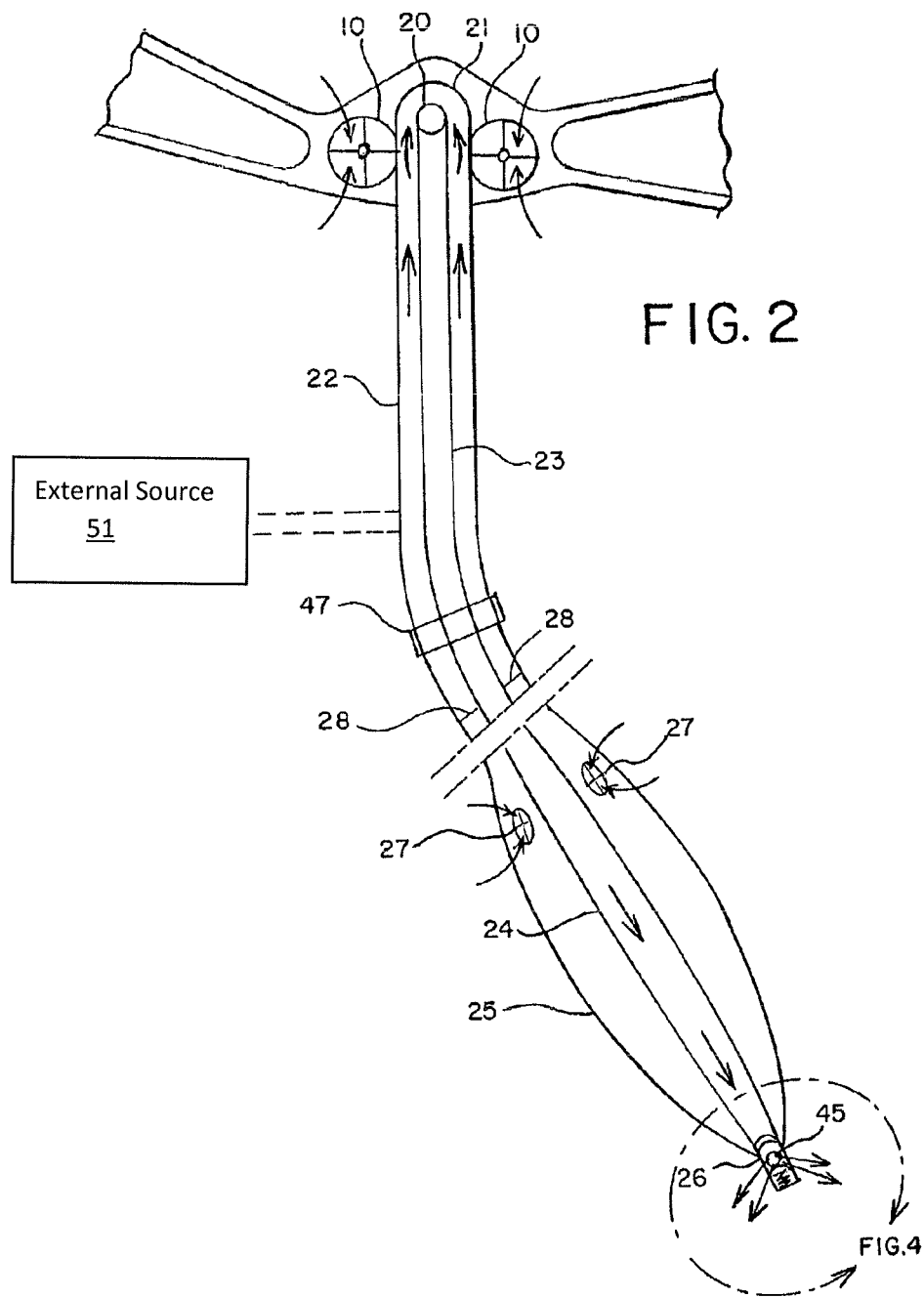
FIG. 2 is a schematic cross-sectional view of the breathing assistance apparatus during an inhalation sequence.

Referring to FIGS. 1, 2, and 26, a breathing assistance apparatus includes a patient interface, shown as a mask 2. In other embodiments, the interface may be configured as a mouthpiece, nasal cannula, mask, or combinations thereof or may include a connector suited for connecting a respiratory tube, such as an endotracheal tube or tracheostomy tube. The interface may include at least one inhalation valve in communication with ambient air. For example, in one embodiment, the mask may be configured with an inhalation valve 21 and an exhalation valve 20, which may be integrally formed in one embodiment, for example as a duckbill exhalation valve and an annular inhalation valve. In one embodiment, the exhalation valve 20 may be removably connected to an adaptor that is suited for connection to an apparatus used to clean and disinfect the expiratory flow path tubing. Various straps 4, such as ear loops, may extend from lateral portions of the mask such that it may be secured to a user. The mask covers the nose of the user, and forms a seal with the user's face. In another embodiment, the mask covers the nose and mouth of the user. The mask may be configured with one or more auxiliary one-way inhalation valves 10 which communicate directly with the ambient environment. The mask may also be configured with an adaptor suited to receive a device intended to monitor inspiratory and/or expiratory pressure.

In one embodiment, the patient interface is a nasal cannula that is configured with two cannulas, each suited for insertion into a patient's nostril. One cannula may be solely suited for expiration and the other for inhalation. Alternatively, each cannula may include two separate flow paths parallel to each other or two separate concentric flow paths with one flow path used as an expiratory flow path and the other as an inspiratory flow path. Each nasal cannula flow path includes a one-way valve to maintain the flow in the flow path in the desired direction. The cannulas may be connected to the expiratory flow path and inspiratory flow path. In one embodiment, the breathing assistance apparatus may include two separate expiratory flow paths and two separate inspiratory flow paths, with each connected to a nasal cannula.

The one-way exhalation valve 20 communicates with an expiratory flow path 23, configured as a tube in one embodiment, upon exhalation by the user. The one-way inhalation valve 21 communicates with an inspiratory flow path 22, configured as a tube in one embodiment, upon inhalation by the user. The proximal portion 67 of the inspiratory flow path tubing closest to the inhalation valve would not be expandable in one embodiment. In order to reduce inhalation effort, the inhalation valve 21 is provided with a larger surface area than the exhalation valve 20 in one embodiment. Of course, it should be understood that the pressure or flow required to open any valve may be adjusted and predetermined by the design and materials of the valve. The one-way auxiliary inhalation valve(s) 10 open to allow the flow of ambient air if and when the pressure drops to negative values in the inspiratory flow path 22, with the auxiliary inhalation valve (s) 10 providing the user with an ample supply of air.

In one embodiment, the expiratory tubing 23 has an inner diameter of about 5 mm, while the inhalation tubing has an inner diameter of about 15 mm. The expiratory flow path 23, or tubing, communicates between the valve 20 and a first location, or inlet, on an inner volumetric member 24, configured in one embodiment as an expandable expiratory balloon or bag. In one embodiment, the expiratory tubing and inner volumetric member may be integrally formed, but each may be made with a material of a different compliance.

An outer volumetric member 25 surrounds at least a portion, and in one embodiment the entirety, of the inner volumetric member 24. In one embodiment, the inner volumetric member is slipped inside the outer volumetric member, which may be resealed. The outer volumetric member 25 may be configured in one embodiment as an expandable inspiratory balloon or bag. In one embodiment, the outer volumetric member 25 has a first volume of about 500 cc when no pressure is being applied thereto. The outer volumetric member 25 may be made of a relatively rigid foam type material that is squeezable by hand, but able to quickly recover a normalized position when released. In one embodiment, the outer volumetric member has a general football shape. One or more intake portals 27 may be located on the outer volumetric member 25. In one embodiment, the portals are configured with one-way valves that allow one-way flow from the ambient environment into the member 25. The intake portals 27 are spaced apart from a pressure relief valve 26 such that exhaled gases exiting the valve 26 are not rebreathed through the portal(s) 27. The outer volumetric member 25 is coupled to the inspiratory flow path 22 such that the member 25 and flow path 22 are in fluid communication. In one embodiment, the outer volumetric member 25 and the inspiratory flow path tube 22 are integrally formed. The outer volumetric member 25 may be provided with straps, buttons, snaps, adhesive or other devices to allow for the apparatus to be secured to the user's chest or other convenient location. In one embodiment, the inner volumetric member 24 has a volume of up to 100 cc when deflated and a volume of up to 500 cc when inflated.

The inner volumetric member 24 has a defined shape memory, and in one embodiment, is configured with a general football shape. In one embodiment, the inner volumetric member 24 is made of an elastic material that expands in response to an increase in air pressure and contracts in response to a decrease in air pressure. Examples of suitable elastic materials include rubber and silicone. The inner volumetric member 24 is coupled to the flow path tube 23 at a first location, whether by way of a connector or by way of an integral, continuous formation, and to the pressure relief valve 26 at a second location spaced from the first location. The pressure relief valve 26 is configured as a pop-up valve in one embodiment.

Figure 3:
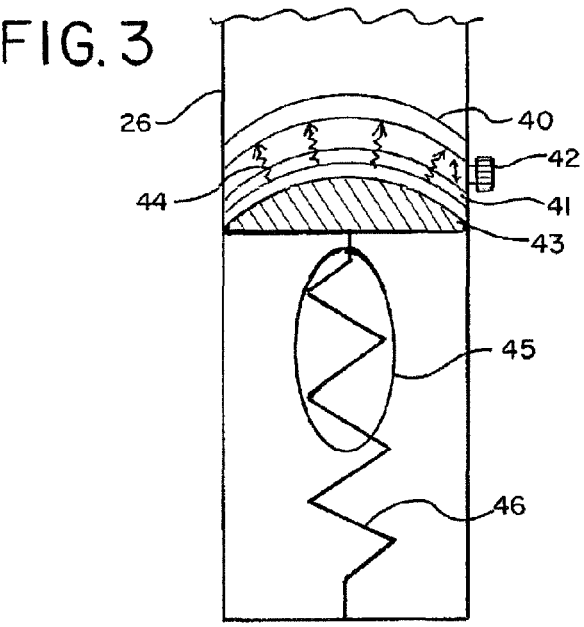
FIG. 3 is a cross-sectional view of one embodiment of an exhalation valve in a closed position.
Figure 4:
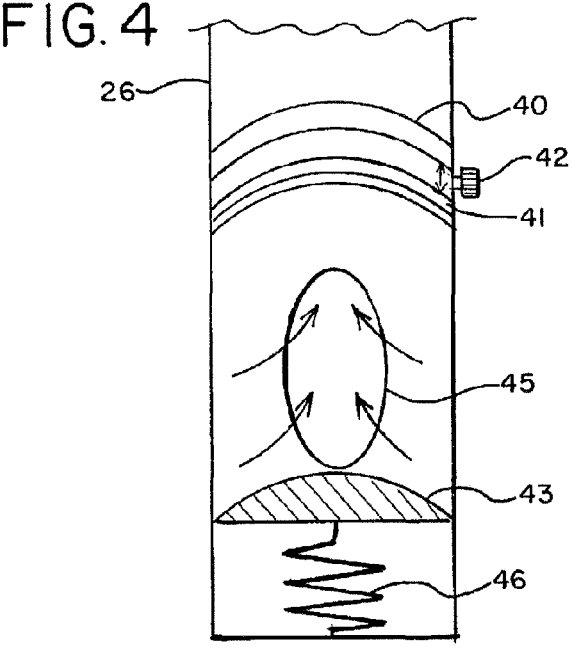
FIG. 4 is a cross-sectional view of the exhalation valve in an open position.
Figure 5A:
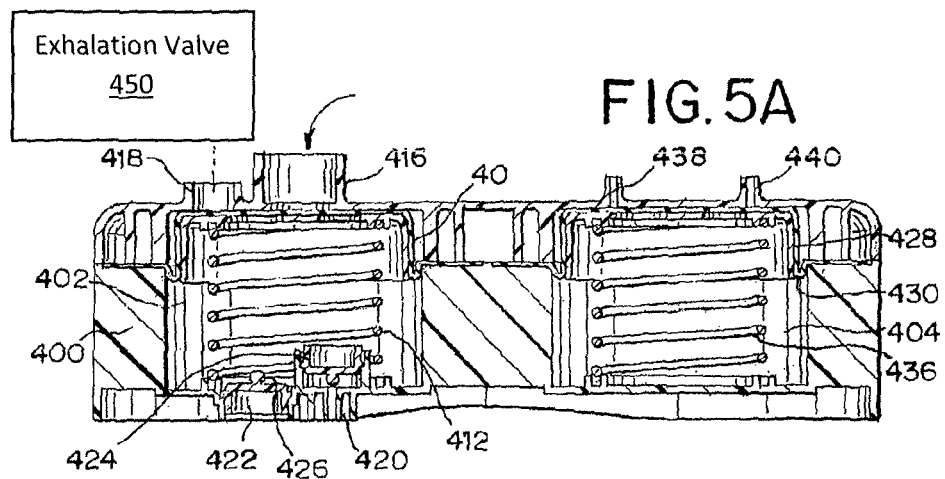
Figure 5B:
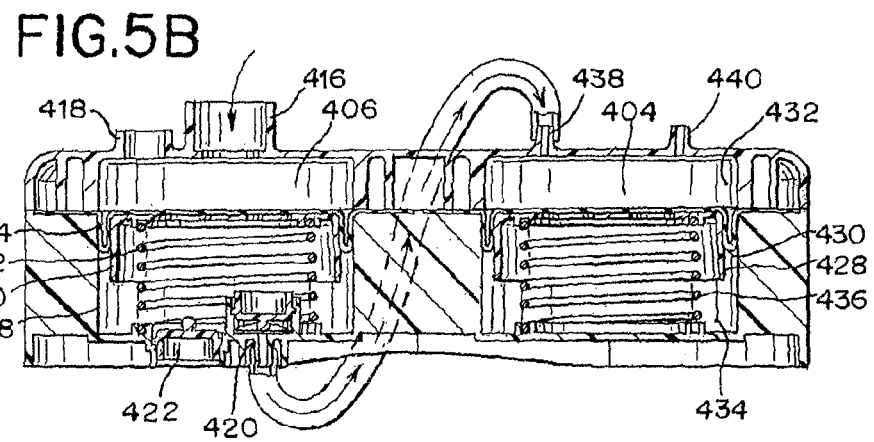
Figure 5C:
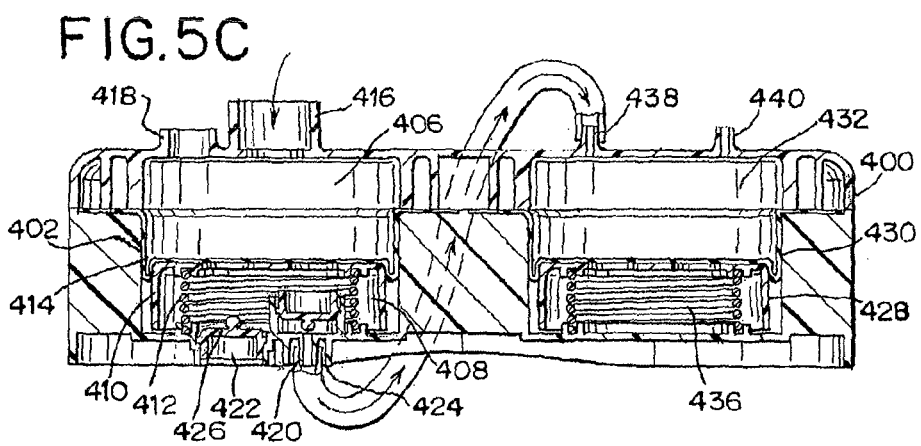

Referring to FIGS. 3, 4, and 27, the pressure relief valve 26 includes a narrow magnetic band 40 spaced apart from a non-magnetic band 41, formed for example from plastic, adjacent an end of the pressure relief valve 26 communicating with the interior volume of the inner volumetric member 24. The spacing between the bands 40, 41 may be varied by a control mechanism 42. In one embodiment, the control mechanism includes a screw that when rotated in a first direction will increase the spacing between the magnetic band 40 and the non-magnetic band 41 and when rotated in a second direction will decrease the spacing between the magnetic band 40 and the non-magnetic band 41. A valve head 43 is made of a metal in one embodiment. In a closed position, shown in FIG. 3, the valve head 43 rests against a valve seat 41. The magnetic force 44 between the band 40 and the valve head 43 is determined by the spacing in between, which may be adjusted by the control mechanism 42. The magnetic force 44 determines the pressure (PEP) required to open the pressure relief valve 26, or move the valve head 43 away from the valve seat 41. The positive pressure required to open the pressure relief valve 26 is preferably between 3 cm $H_2O$ and 30 cm $H_2O$, and in one embodiment, between 10 cm $H_2O$ and 30 cm $H_2O$. In one embodiment, a connector may be placed between the proximal portion of the pressure relief valve 26 and the distal end of the inner volumetric member 24. The connector is suited to receive a device used to monitor expiratory pressure.

When the exhalation pressure exceeds the predetermined magnetic force 44, the exhalation flow pushes the valve head 43 down and maintains such a position so as to allow the exhalation gases to pass or escape through one or more openings 45 to the ambient environment. The valve 26 remains open as long as the exhalation pressure exceeds the return force of an adjustable spring 46. The return force of the adjustable spring 46 may be set at a force between about 0.1 cm $H_2O$—up to 30 cm $H_2O$, preferably between 1 cm $H_2O$—up to 10 cm $H_2O$, and most preferably between 1 cm $H_2O$—up to 5 cm $H_2O$. Typically, the valve 26 opens, or is activated, at the end of the exhalation sequence, thereby providing for synchrony between the opening and inhalation. One can vary the valve 26 opening onset by modifying the ratio between the user's normal tidal volume and the inhalation tubing 22 volume capacity, for example by adjusting a choke 47 fitted around the tubing 22 as shown in FIGS. 1 and 2. The choke 47 may be adjusted to accommodate users with different tidal volumes. If a user has a low tidal volume, the choke 47 will be adjusted to decrease the volume capacity of the inspiratory flow path tubing 22 in order to accommodate the lower tidal volume of the user. In another embodiment, the volume capacity of the inspiratory flow path tubing 22 may be adjusted automatically to accommodate the lower tidal volume of the user. The volume capacity of the inspiratory flow path tubing 22 should ideally be slightly lower than the tidal volume of the user to reach the necessary pressure to open the pressure relief valve 26. If, in an exceptional case, a user's tidal volume does not exceed the inhalation tubing 22 capacity, the pressure relief valve 26 may not open, such that the volume in the inner volumetric chamber 24 is maintained. Upon the next exhalation sequence, the pressure relief valve 26 will open if the requisite pressure is reached, allowing virtually all of the exhalation gases to escape thereby decreasing the volume and pressure transmitted to the inhalation tubing 22. The pressurized cycle will then resume with the next normal tidal volume from the user. A normal tidal volume of a user is a volume that corresponds to the volume capacity of the inspiratory flow path such that the volume of the inspiratory flow path is slightly lower than the normal tidal volume.

In one embodiment, the shape of the volumetric members 24, 25 may be flattened and hidden under a garment. During inhalation, the user may simply squeeze the outer member 25 between an arm and chest for inhalation assistance. In one embodiment, the outer volumetric member 25 is about 15 cm long×8 cm wide×4 cm thick when no pressure is being applied. In another embodiment, the inhalation tubing 22 may be placed around the abdominal area or thoracic area to enhance inhalation assistance. An enhanced assistance results from the extra pressure provided by the thorax expansion observed during inhalation attempts against obstructed airways.

In operation, during exhalation as shown in FIG. 1, the intake valves 10 are closed and all exhaust or expiratory gases are passed through the valve 20 and the flow path 23 and into the inner volumetric member 24. When a predetermined pressure is realized by the exhaled gas in the inner volumetric member 24, the pressure relief valve 26 opens and releases the gases to the ambient environment. The pressure relief valve 26 is configured to provide a positive expiratory pressure (PEP). As the exhalation gases enter the inner volumetric member 24, the volume of the inner volumetric member 24 increases, or the balloon inflates, with the inner volumetric member 24 applying a pressure to the interior wall of the outer volumetric member 25, thereby pressurizing the gases, or air, in the outer volumetric member 25. In one preferred embodiment, the outer volumetric member 25 has a lower compliance than the inhalation tubing 22. In one preferred embodiment, the expandable portion of the inspiratory flow path tubing 22 has a compliance of about 50 cc/cm $H_2O$, the expiratory flow path tubing 23 is made of a non-compliant material, the inner volumetric member 24 has a compliance of about 75 cc/cm $H_2O$, and the outer volumetric member 25 has a compliance of about 5 cc/cm $H_2O$. The positive pressure in the outer volumetric member 25 during the exhalation sequence is passed on to the inspiratory flow path tubing 22, with a one-way valve 28 positioned at the junction between the outer volumetric member 25 and the inspiratory flow path tubing 22 maintaining the collected pressure. The junction portion where the one-way valve is located is made of a non-compliant material. The one-way valve 28 allows for air to migrate from the outer volumetric member 25 to the inspiratory flow path tubing 22, but does not allow air in the inspiratory flow path tubing to migrate back into the outer volumetric member 25 thereby maintaining the inspiratory flow path tubing in a pressurized state to assist with inhalation. In one embodiment, a plurality of one-way valves is located at the junction between the outer volumetric member 25 and the inspiratory flow path tubing 22.

Referring to FIG. 2, during inhalation, the resiliency of the outer member 25 and the inhalation tube 22 provides a positive pressure to the air flow during the inhalation sequence through the one-way inhalation valve 21. During the inhalation sequence, the positive pressure may drop in the outer volumetric member 25 and the inhalation tubing 22, such that a slight negative pressure may be realized. Ambient air is then drawn in through the auxiliary valve(s) 10 located on the patient interface, and through the intake portals 27 communicating with the outer volumetric member 25. During the inhalation sequence the inner volumetric member 24 is emptied so as to be ready for filling on the next exhalation sequence. The level of positive pressure applied to the outer volumetric member 25 and inspiratory flow path 22 by the inner volumetric member is adjusted via the control mechanism 42. If the user talks or breathes out through their mouth while wearing a nasal mask, a temporary loss of positive pressure may result but will resume on the next nasal exhalation sequence.

The apparatus and method of use allow for the warmed exhalation gases to flow along the centralized expiratory flow path 23, with the inhalation gases flowing along the inspiratory flow path 22 being warmed thereby, which may benefit users sensitive to cold air. In addition, hydrophilic material may be used for the expiratory flow paths 23, 24 to help humidify the inhalation gases.

The apparatus and method provide for several types of positive airway pressure. For example and without limitation, the pressure relief valve 26 provides for positive expiratory pressure (PEP) during the exhalation sequence, with the elasticity of the inner member 24 and the variable exhalation valve 26 preventing pressure spikes in the lungs of the user. The PEP may be used to treat snoring, obstructive sleep apnea, asthma, COPD, hypoxemia, atelectasis, CHF, bronchial congestion, high altitude sickness, and variations or combinations thereof.

The apparatus and method also provide positive pressure during the inhalation sequence, primarily at the beginning of the inhalation sequence. While the pressure may actually drop to a slightly negative pressure, the initial push at the commencement of the inhalation sequence is significant and helps to prevent the small airways from closing especially during the first third of the inhalation sequence. In addition, a prescribed $O_2$ flow may be introduced into the flow path 22, for example from an external source 51 communicating with the flow path 22, so as to sustain the positive pressure during inhalation while a high $O_2$ concentration is delivered at the crucial beginning of the inhalation sequence, thereby improving the $O_2$ therapy efficiency. In this way, conventional $O_2$ therapy may be reduced, or eliminated altogether. Other gases may be introduced into the flow path 22 from an external source 51 which is in flow communication with the flow path 22 via a connector. The same connector may also be used to connect a device for monitoring the inspiratory pressure. Another connector may be used to introduce into the flow path 22 an aerosolized substance, such as an aerosolized medicament.

In order to maintain a manual CPAP, the user, or a caregiver, may gently squeeze the members 24, 25 in sequence with the user's inhalation pace. The apparatus may also be used as a breathing exerciser for COPD and degenerative muscular disease patients to facilitate bronchial hygiene and to prevent atelectasis. In order to obtain a full CPAP, an external source of gas (air or mixed air/$O_2$) may be introduced into the flow path 22 to keep it pressurized, even at the end of the inhalation sequence. Finally, the apparatus, with the pressure relief valve 26, may be used for manual ventilation in case of respiratory arrest. A choker 47 is used to adjust the inhalation tubing 22 to minimize the expandable portion of the inhalation tubing 22 such that the air transmitted from the outer volumetric member 25 is immediately transmitted to the patient. In another embodiment, an inflatable portion of the inspiratory pathway 22 contains pliable foam or other pliable material that maintains a residual volume of about 100 cc when no pressure is applied. The inflatable portion of the inspiratory pathway 22 is fastened between an adjustable band and the user's thorax. The band encircles the user's thorax and may be adjusted to apply pressure over the user's thorax. During inhalation, the thorax expands diametrically causing compression of the inflatable portion of inspiratory pathway 22 against the band, thereby maintaining a positive pressure inside the inflatable portion of the inspiratory pathway 22. If a larger than normal inhalation occurs, the thorax expands further thereby maintaining pressure on the inflatable portion of the inspiratory pathway 22 while expelling residual air. During exhalation, the inflatable portion of the inspiratory pathway 22 inflates and maintains a positive pressure thereby maintaining contact with the retracting thorax. If a larger than normal exhalation occurs, the thorax will retract further providing the inflatable portion of the inspiratory pathway 22 with more room to expand and maintain contact with the user's chest thereby promoting a more complete exhalation. This embodiment allows inflation and deflation of the inflatable portion of the inspiratory pathway 22 in a manner that corresponds with the expansion and retraction of the thorax thereby automatically adjusting the user's tidal volume to the inflatable portion of the inspiratory pathway 22 air capacity as restrained by the pressure relief valve 26. Furthermore, if in spite of using the breathing apparatus a complete obstruction occurs, such as during obstructive sleep apnea, the thorax expansion during an inhalation attempt will increase the pressure in the inspiratory pathway 22 thereby assisting to unblock the airway passage to resume normal breathing.

Now referring to FIGS. 26 and 27, a control 48 is provided underneath the expiratory valve 26 and is coupled to the spring 46, such that the pressure of the spring 46 may be adjusted against the head valve 43. That pressure builds the end expiratory pressure (PEEP), which is also bound to a residual volume accumulated in balloon (A).

Figure 28A:
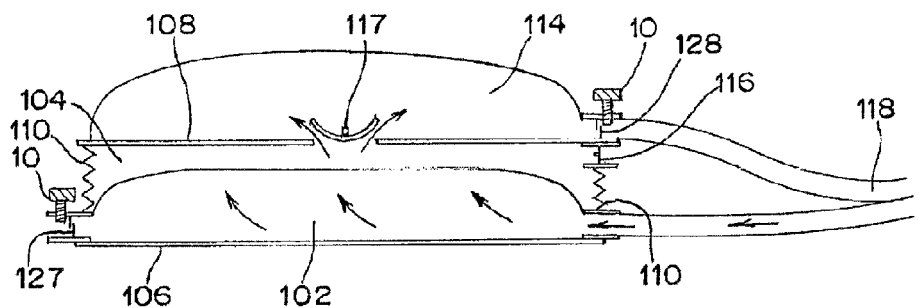
Figure 28B:
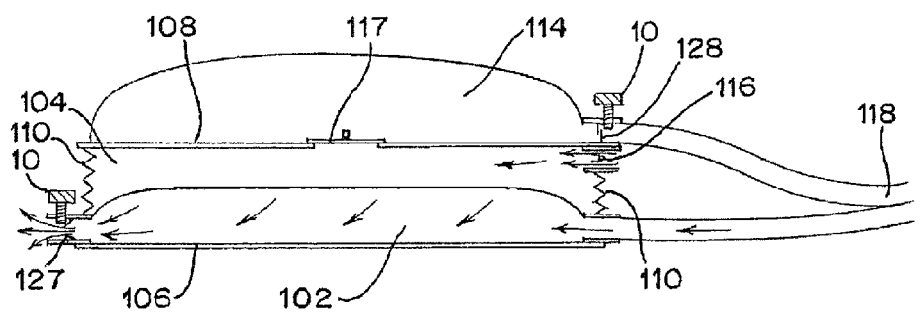
Figure 28C:
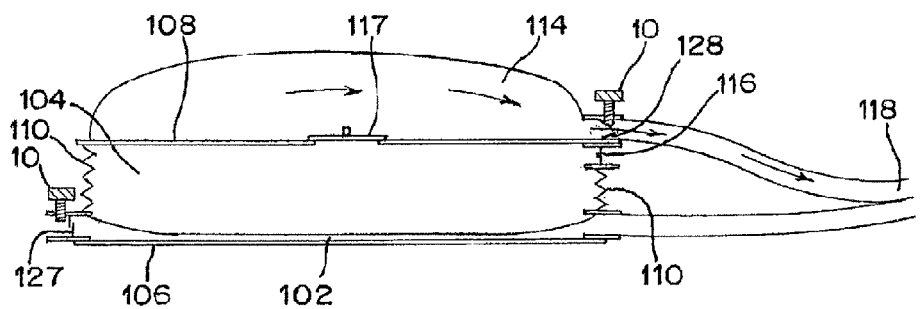
Figure 28D:
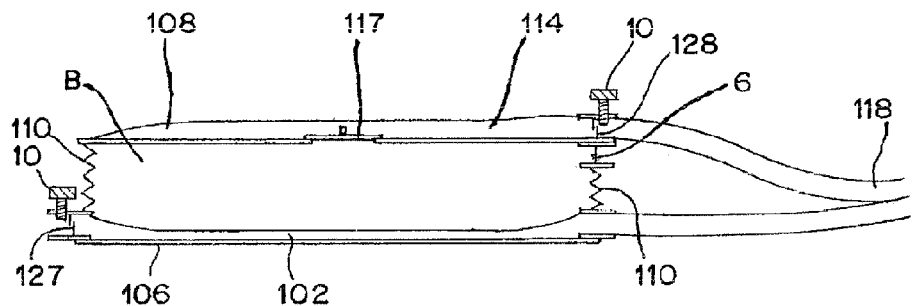
Figure 28E:
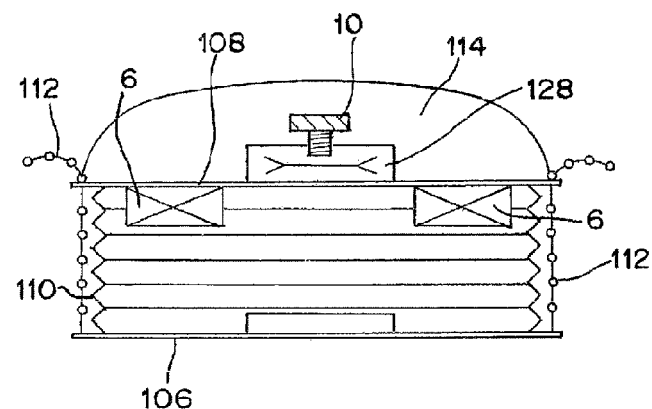
Figure 28F:
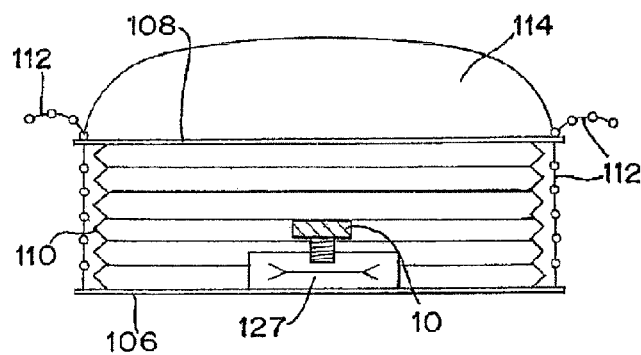
Figure 33A:
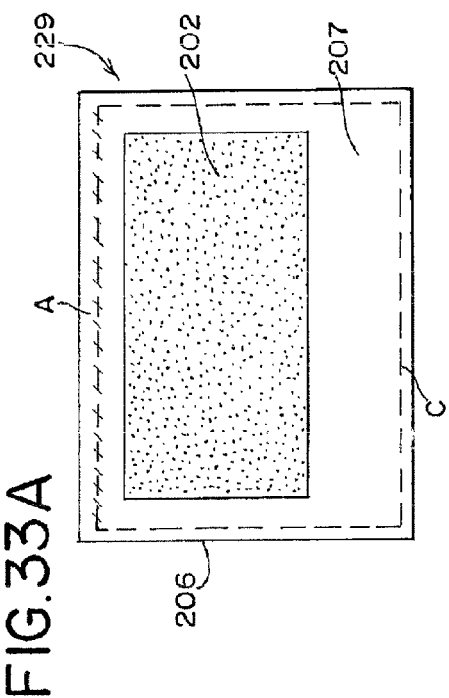
FIGS. 33A and B show the operation of a valve.
Figure 33B:
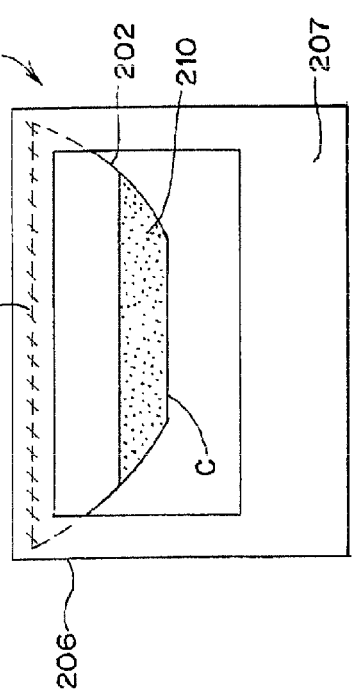
Figure 32:
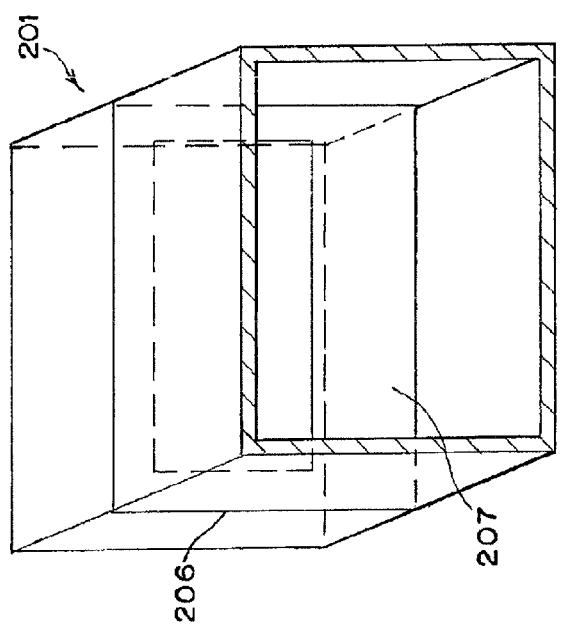
FIG. 32 shows a frame for a peak pressure and PEEP valve.
Figure 34:
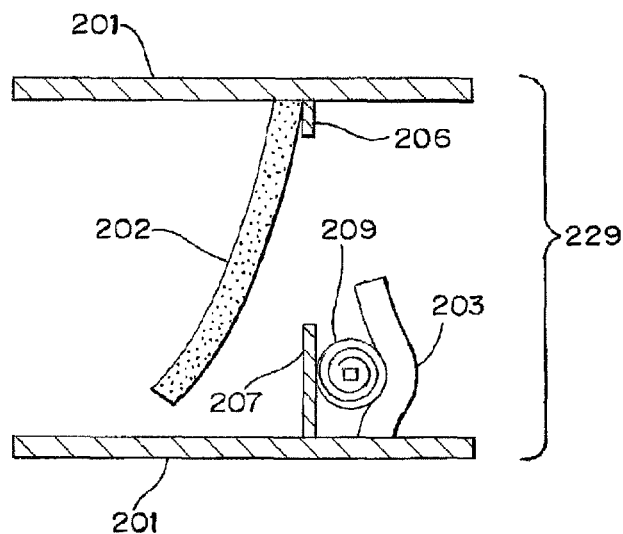
FIG. 34 is a side view of the valve shown in FIG. 32.

In the embodiment of FIGS. 28A-29, the volumetric member 102 is emptied with each breathing cycle in spite of a lasting air flow resistance. To accomplish this, the volumetric member 102 is configured as resilient balloon, which collapses under a certain pressure. The minimum pressure required to keep the member 102 inflated is defined as the "closing pressure". Once the closing pressure is exceed(ed), the member 102 will inflate much more easily, requiring less and less pressure for an increasing volume of air. This type of non-linear compliance is exemplary of the response of a latex type balloon whose membrane gets thinner and thinner as it inflates. Member 102 fully empties with each exhalation, in spite of a low pressure maintained by the expiratory valve 26 throughout the exhalation phase (PEEP). In order for member 102 to deflate completely towards the end of the patient's exhalation, a closing pressure must exceed the pressure created by the control 48 on the head valve 43 (PEEP).

The member 102 is inserted into a volumetric element, or housing 104 in an airtight way as shown in FIGS. 28A-D and 29. In one embodiment, element 104 may be represented as a rectangular box, dimensioned for example as 3 inches×5 inches×4 inches" (about 8 cm×13 cm×2 cm), or having a volume of about 150 cc. In other embodiments, the volume is between about 185 and 200 cc, or as much as 500 cc. The element 104 has a base 106 and top 108, which may be similar, rigid, plastic plates 106, 108 connected in an airtight fashion by resilient elements 110 built into or added to a material lining. The plates 106, 108 are kept distant from each other by the force of the resilient elements 110. This resilience should allow the member 104 to be hand-squeezed if needed, so to permit additional inhalation assistance. Furthermore, it will be possible, by pulling and fastening a catch mechanism, such as a knotted string or plastic element 112 or other fastener system, to fully squeeze the member 104 so as to temporarily reduce the thickness of element 104 to about ½ inch for shipping purposes or to make it more portable between uses. It will also be possible to only slightly diminish or increase the member 104 capacity by adjusting the member 104 volume via the adjustment member 112 or other fastener. This will allow the user to adjust the volume of the member 104 to the right size that is needed in order to match the selected parameters.

For example, with volumetric elements 102 and 114 having an initial compliance of 20 cc/cm H2O coupled to a valve 26 with an opening pressure of 5 cm H2O, the capacity of member 104 may be reduce to a less bulky 50 cc. With members 102, 114 coupled to a valve 26 having an opening pressure of 8 cm H2O, the capacity of member 104 may need to be increased to about 80 cc. For a valve 26 with an opening pressure of 10 cm H2O, the volume of member 104 may need to be increased about 100 cc, and so on. The expandable member 104 allows for changing the size of the device for a customized use, thereby providing for and covering the needs of a variety of pediatric, OSA, COPD patients, as well as any end users desiring further performance.

The variation of the opening pressure of the expiratory valve 26 and/or its PEEP allows for modulating the expiratory pattern in order to match individual needs. On the other hand, a full range of volumes and pressures for inhalation assistance can be achieved by varying the opening pressure of the valve 26 and/or the compliance of elements 102 and 114. If desired, the compliance of element 102 can be reduced by the adjustable element 104. For element 114, compliance may be reduced via a plastic plate 191 as shown in FIG. 29, which may be secured to the top 108 of member 104, so as to restrict the capacity of member 114.

Member 104 is supplied with one or more one-way valve(s) 116 for fresh air intake, with the aperture also protected by a filter if desired. The member 114 is positioned in an airtight relationship adjacent member 104 to which it is coupled via one or more one-way valves 117. Member 114 may be configured with the same shape, e.g., rectangular in one embodiment, that corresponds to the shape and size of member 104. When member 114 is inflated, the thorax in the expiratory phase is retracted, minimizing the noticeable bump of the device, which may be hidden under a garment in any case. Referring to FIG. 30, the diameter of the tubing 118 coupled to members 102 and 114 may be reduced from 17 mm OD to 16 mm OD by utilizing a double lumen tubing, with ⅓ of the flow path 119 being used for exhalation and ⅔ of the flow path for inhalation 113.

In operation, upon exhalation through the ⅓ passage way of tube 118, and through member 102, the internal pressure increases over its closing pressure (e.g., 6 cm H2O) and keeps increasing while member 102 inflates up to the opening pressure of valve 26 (e.g., 10 cm H2O). During that time, atmospheric air maintained within the rigid but squeezable member 104 is passed on to member 114 through a one-way valve(s) 117. Then the valve 26 opens, and the pressure drops gradually to the PEEP level adjusted via control 48 (e.g., 4 cm H2O). During that time, member 102 deflates along with the user's exhalation through valve 26, while member 104 is filled with fresh air admitted through the one-way valve(s) 116. Because of the concept of communicating vessels, the initial pressure of 10 cm H2O in member 114 may tend to leak into the expiratory pathway, which ends with a PEEP of 4 cm H2O.

To save the built up pressure and volume contained within the inhalation pathway, a one-way valve 129 as shown in FIGS. 31A-C may be used. The amount of resilience of diaphragm valve 129 may vary with the elasticity of the material, surface, thickness and the layout of slits 121. The resilience may be preset, for example by using pair of valves 129 with matching pressures. These valves 129 are made to easily connect and disconnect from the outlets 127, 128 of members 102 and 114 respectively. The resilience of the valve 129 may be adjustable, for example via an adjustment device such as a screw 124 that moves in front of a portion of the diaphragm 125 in order to limit, to a certain extent, the opening of the slits 121. This system allows for an initial inhalation pressure that is higher than the PEEP, which permits a bi-level positive airway pressure or a similar BPAP mode. The split resilient diaphragm valve 129 has a defined resistance to air flow opening and another defined resistance to air flow closing. In other words, the required pressure to open the diaphragm valve 129 will be higher than the pressure to keep it open. The resistance of the valve 129 in outlet 128 may need to be tuned with the resistance of the valve 129 in the outlet 127. For example, to synchronize the opening pressure of the inhalation valve 129 in outlet 128, the adjustment member 124 may be adjusted to the point of self-opening of the inhalation valve 128 (without any inhalation effort) and then backed off slightly in order to find a comfortable trigger level. The valve 129 has fewer parts, is less expensive to manufacture, and may be more reliable.

COPD patients may become fatigued in trying to reach a peak pressure at the end of their exhalation. Indeed, the expiratory muscles' strength is lowest at that point of the exhalation cycle. The full strength of the expiratory muscles is exhibited at the beginning of the exhalation, while the lungs are stretched. Passive exhalation already provides some positive pressure, which users can amplify to build a higher peak pressure while their expiratory stroke is at its maximum. It will likely require the first third of their exhalation to assist the first third of their inhalation. COPD patients will benefit the most from this energy swing between their well braced expiratory muscles and their strained inhalation muscles. In addition to the positive airways pressure effect, this expiratory saved energy represents a significant reduction of the work of breathing for a COPD patient.

Expiratory vibrations may also improve gas exchange. Such vibrations are possible through the diaphragm valve(s) 129 or via stretched thread(s) inserted into portion(s) of enlarged, somewhat rigid tubing suited to create beneficial vibrations transmitted to the lungs (not illustrated).

Referring to FIGS. 32-35, another valve 229 provides independent control over Peak Pressure and PEEP. The valve 229 is provided with two controls: one to adjust its opening pressure and another one to adjust its closing pressure. Therefore, this valve 229 allows for an independent control of the Peak Pressure reached within members 102, 104 and 114 and for an independent control of the PEEP in member 102.

The valve 229 may include a rigid, plastic, rectangular frame 201, a latex type diaphragm valve 202 disposed within the frame 201, a magnetic strip 203, and adjustment members, configured as screws 204, 205 that are used as control devices to regulate the diaphragm 202 shift. In one embodiment, the frame 201 has dimensions of about 2 cm×1.5 cm ID×2 cm depth, with an inner stop 206 located between the two ends. The stop provides three sides or surfaces, which are about 2 mm wide, and a bottom surface 207, which is longer, e.g., about 5 mm wide. One edge of the valves 202 is fastened to the stop, with a free end of the valve disposed adjacent the larger stop surface 207, allowing the valve to pivot or rotated about the edge thereof.

When the valve 202 is at rest, e.g., when no pressure is being applied, the valve will lie flat against the stop 206, which serves as a valve seat. In order to maintain the air tightness in spite of an upstream positive pressure, a control is provided to control the amount of required pressure to move the valve 202 from the stop or seat 206. The control may include an adjustable magnetic force.

In one embodiment, the magnetic force may be applied by a flexible or semi-flexible, magnetic strip 203 facing the stop surface 207, on the same axis. For example, the magnetic strip 203 may be about 20 mm×7 mm. The strip 203 is fastened to the frame 201 at a distance of about 2 mm, proximally from the stop surface 207. This 2 mm gap allows for an adjustment device, shown as a plastic screw shaft 209 to slide along the same axis, and between the stop surface 207 and the magnetic strip 203 as to vary the space between them. The shaft 209 is about 3 mm OD for diameter and up to 20 mm long, and may be provided with code indicators.

The valve 202 may be configured with metal elements in it or with a metal band 210 positioned on the proximal surface of the valve, in order to make the diaphragm 202 attractive to the magnetic strip 203. If used, the metal band 210 may be about 20 mm by 5 mm. In order to maintain an air tight seat to the valve 229, the attractive forces should be capable of being applied through the thickness of the stop 206. The stop 206 may be metalized if needed. The attractive forces should be strong enough to make the flexible magnetic strip 203 bend towards the metalized valve 202 at rest unless the adjustment device, e.g., screw shaft 209 is introduced between them. The attractive forces applied to the diaphragm valve 202 determine the opening pressure or Peak Pressure which may vary from 0 to about 50 cm H2O and preferably from 3 to about 20 cm H2O.

Even when the adjustment device 204 is not acting on the valve 202, it should remain fixed to the frame to avoid misplacement. The adjustment device may be provided with a grippable member 211, or a member capable of being actuated with a tool, such as a screw driver or Allen wrench.

In alternative embodiments, the magnetic force may be varied via an optional electric module (battery operated). This module may, for example, automatically increase the Opening Pressure if the valve 229 does not open for determined laps of time following repeated obstructive apneas.

Figure 35:
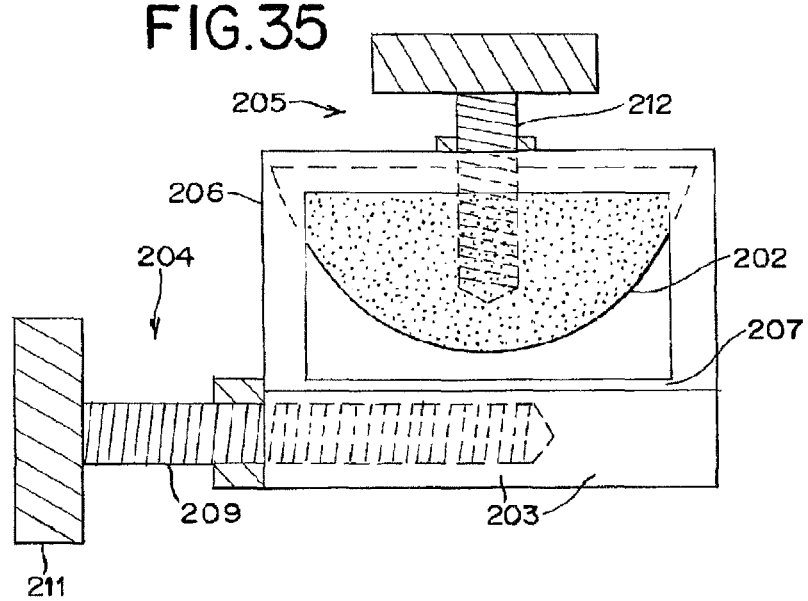
FIG. 35 show a control for the valve shown in FIG. 32.
Figure 37:
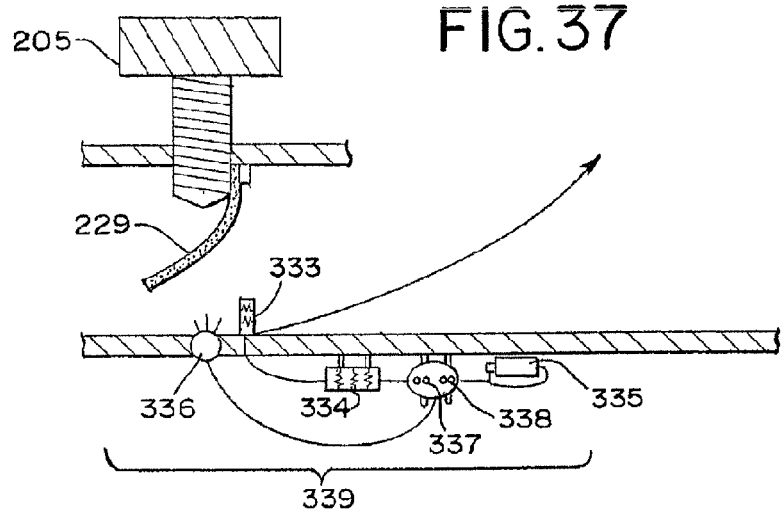
FIG. 37 shows a valve control embodiment.

The closing pressure may be adjusted via adjustment device 205 located downstream of the diaphragm valve 202, e.g., about 2 mm, as shown in FIGS. 35 and 37. In one embodiment, the adjustment device 205 includes a screw shaft 212, e.g., about 3 mm OD diameter and 10 mm long, projecting inwardly into the flow path defined by the frame 201. When the valve 229 opens, the valve 202 engages the shaft 212, which impedes the bending and flexing of the valve. The portion of the diaphragm 202 that is engaged by the adjustable shaft 212 length will vary the recall memory of the diaphragm 202 and consequently the Closing Pressure or PEEP. The adjustment device, e.g., the screw 212 may be provided with code indicators. The corners of the valve 202 not supported by the shaft 212 will bend more freely in presence of high pressure, therefore dynamically preventing bursts of pressure.

The valve 229 provides for different users to choose the fraction of their expiration that will be used to assist the subsequent inhalation. Therefore, one can choose to use the first third, the first half, or the almost totality of their expiration to assist inhalation. In addition, regulation of PEEP is performed independent of the Peak Pressure and can be adjusted as needed. When positioned at the member 114 outlet 128, the Peak Pressure control allows for precisely choosing the requested inhalation effort to trigger the valve's 229 opening, while the positive airways pressure is still sustained. For its part, the closing pressure control allows the user to modulate the inhalation flow assistance. Indeed, the user can choose how the volume of inhalation assistance is delivered; either with a burst of air at the beginning of the inhalation, extended during a fraction of, or during the entire inhalation.

Figure 36A:
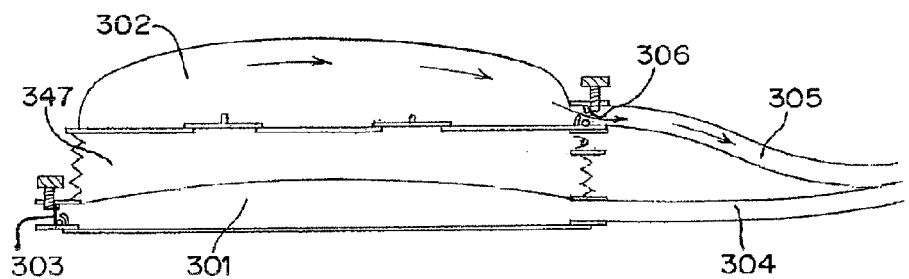
FIGS. 36A and B show an alternative embodiment of a breathing assistance device.
Figure 36B:
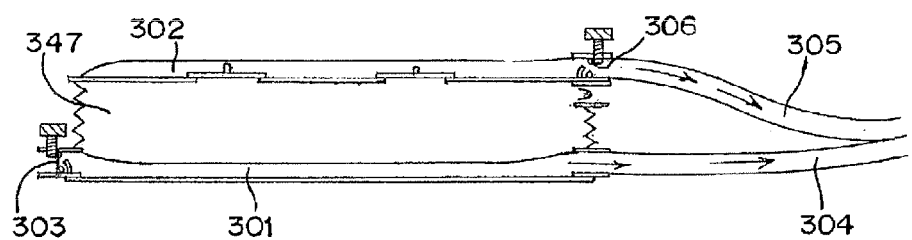

The present embodiment of FIGS. 36A and B allows permissive hypercapnia as there is no one-way valve between member 301 and the patient interface. Member 301 may have a more linear compliance such as the one found with typical black anesthesia bags. The expiratory member 301 emptying will in fact be completed by the user. Doing so will permit some CO2 re-breathing. There are some physiological effects of permissive hypercapnia. For example, it shifts the oxyhemoglobin dissociation curve to the right thereby providing better O2 release at the tissue level. In addition, it provides a bronchodilator, which eases work of breathing, and a vasodilator, which improves cardiac output. In addition, minute ventilation may increase, which tends to lessen hypopnea. It may also provide an anti-inflammatory agent. All those physiological effects are beneficial for patients who are suffering from a respiratory ailment, such as COPD, or those who want to enhance their aerobic capacity.

Figure 43:
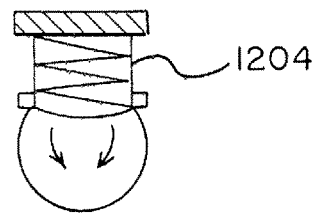
FIG. 43 is a front view of an alternative with the control stem in an open position.
Figure 44:
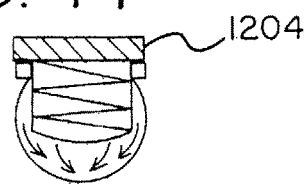
FIG. 44 is a front view of the control stem in a partly closed position.
Figure 45:
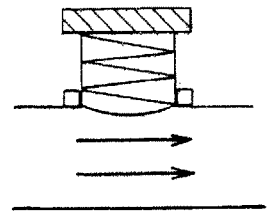
FIG. 45 is a side view of the control stem shown in FIG. 43.
Figure 46:
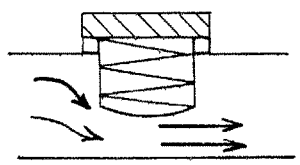
FIG. 46 is a side view of the control stem shown in FIG. 44.

Referring to FIGS. 43-46, the adjustment members 204, 205 may be replaced by a single adjustment member 1204 positioned further from the valve 202, e.g., 5-6 mm, rather than 2 mm, such that the control member 1204 does not contract the valve 202 when in the open position, as shown in FIGS. 43 and 45. The diameter of the adjustment member 1204 may be larger, e.g., 7 mm, instead of the suggested 3 mm for the screw shaft 212. The larger diameter allows the adjustment member 1204 to partially obstruct the inhalation tube, which is about 10 mm in one embodiment. The further the adjustment member 1204 is screwed, or otherwise extended, into the inhalation pathway, the more the adjustment member 1204 reduced the orifice through which the pressurized volume of air travels. Consequently, the user may adjust the flow of inhaled air without a broad range so as to better assist the inhalation. Indeed, the flow may be adjusted from a burst of air at the beginning of the inhalation to light flow, based on the choice and need of the user. The adjustable, restricting airflow adjustment member 1204, or valve, may be positioned at the outlet to create a variable back pressure upon exhalation. For a given size orifice, the expiratory flow rate will influence the amount of back pressure and so the positive pressure built in the member 102 fills the element 114 with pressurized volume of fresh air. Therefore, by changing their expiratory flow rate, the user may gain an additional control of their peak pressure and inhalation control. The expiratory flow rate automatically follows the user's level of activity, with the higher the volume minute, the higher the positive pressure. If the pressure in element 102 drops under a desired level of PEEP at the end of a prolonged exhalation, the stored pressurized volume in element 114 will be released, providing a signal to the user to inhale. Because the user draws in pressurized air from element 114, the air from element 114 will flow to the user's airways, rather than escaping through the outlet of element 102 located further away and having an airflow restriction. The user may also temporarily and/or partially block the outlet of element 102 with a finger to increase the Peak pressure, independently of the expiratory airflow to increase the inhalation assistance.

Figure 39:
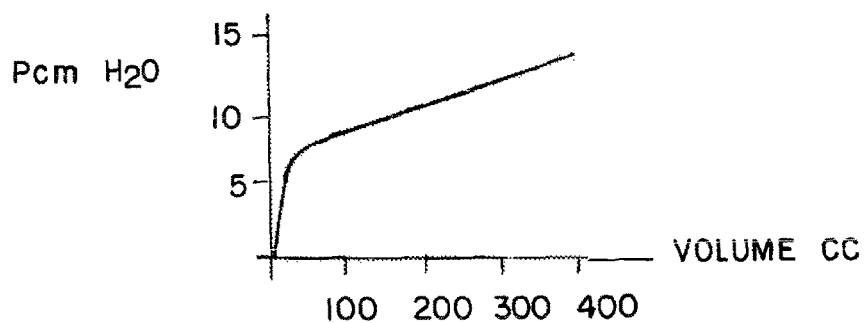
FIG. 39 is a pressure v. volume graph for one embodiment of a breathing assistance device.

Referring to FIGS. 39-42C, different mechanism embodiments are provided to assist in the emptying of the various volumetric elements, including for example and without limitation element 102, 301, between exhalations. Referring to FIG. 39, in a first embodiment, the element 102, 301 may be made of a balloon or bellows with a non-linear compliance. The compliance may correspond for example for the first 50 cc of exhalation to a raise in pressure from 0 to 8 cm $H_2O$ (or 1 cm $H_2O$ over the PEEP), with the balloon releasing and the compliance raises to about 100 cc/cm $H_2O$ or more.

Figure 40A:
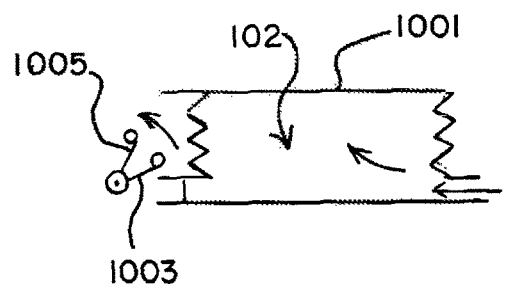
FIGS. 40A and B are schematic views showing a mechanism for emptying a chamber.
Figure 40B:
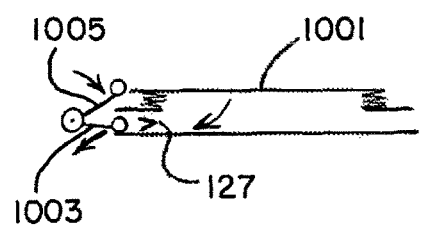
Figure 41:
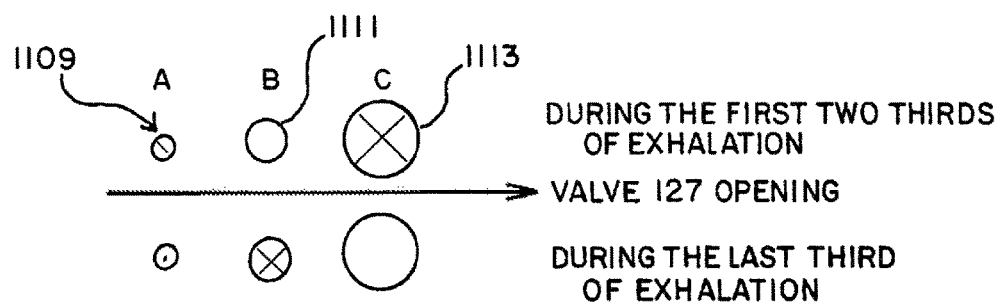
FIG. 41 shows a schematic view of a three-way valve.

Referring to FIGS. 40A and B, an adjustable mechanism can be actuated by a portion, e.g., top, of the element 102, 301 raising with exhalation.

When a maximum pressure is reached, valve 127 opens and the element 102 starts to deflate. In response, a rigid top 1001 presses down on a lower arm 1003, rotating the arm. Stored energy in the mechanism is released and an upper arm 1005 presses down on the element 102 to complete the emptying thereof.

In the embodiment shown in FIGS. 41 and 47-54B, a three way valve initially allows expiratory air flow through opening 1111 to inflate the element 102. Once the maximum pressure is reached, the valve 127 opens and the expiratory air flow is redirected to a restrictive outlet 1109 to create a PEEP. At the same time, a second larger outlet 1113 is opened allow a quick, free emptying of element 102. The outlet 1113 facilitates the emptying of the element 102.

Outlet 1109 is a high resistance port that connects the patient's expiratory flow to atmosphere, and outlet 1113 is a low resistance port that connects the exhalation membrane to atmosphere. At the beginning of exhalation, outlets 1109 and 1113 are closed, and outlet 1111 is opened, resulting in all expiratory flow being directed into the exhalation membrane and charging the system. Once a peak pressure is reached, the outlet 1111 is closed, and outlets 1109 and 1113 are opened, thereby diverting all of the remaining expiratory flow from the patient to atmosphere through outlet 1109, with the high resistance maintaining PEP and also allowing the exhalation membrane to deflate completely through the low resistance outlet 1113. Outlet 1109 closes at the desired PEEP level, similar to other exhalation valves disclosed herein.

Maintaining residual volume in the inhalation membrane after each assist greatly improves the efficiency of the system, because opening and closing the membrane wastes energy, and may shorten the life span of the membrane.

Inflation and deflation of an elastic membrane follow different paths on the pressure-volume curve due to hysteresis and as a result, the closing pressure of the membrane is slightly lower than its opening pressure. Using a pressure sensor, electronic solenoid valve and control system, the inhalation port is opened when PEEP is reached to commence inhalation. As the pressure in the inhalation membrane rises, since the membrane is decreasing in volume as the patient inhales, the pressure is continuously monitored and when a threshold just below the membranes closing pressure is reached, the inhalation port is closed. This maintains the membrane at a volume above its closing volume.

Figure 47:
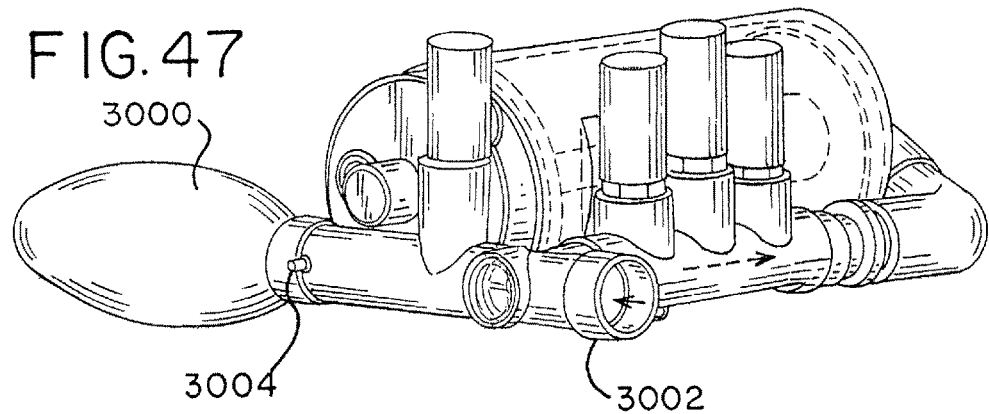
FIGS. 47-48 show an embodiment of a breathing assistance device in isometric and cut-away views.
Figure 48:
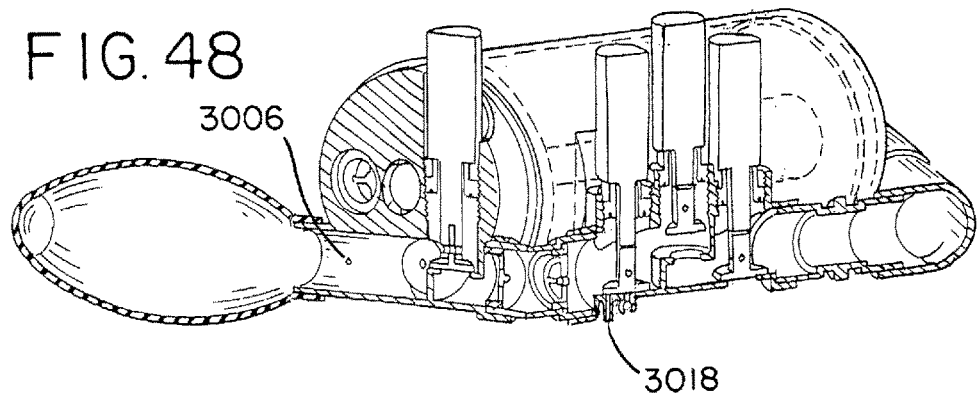
Figure 54A:
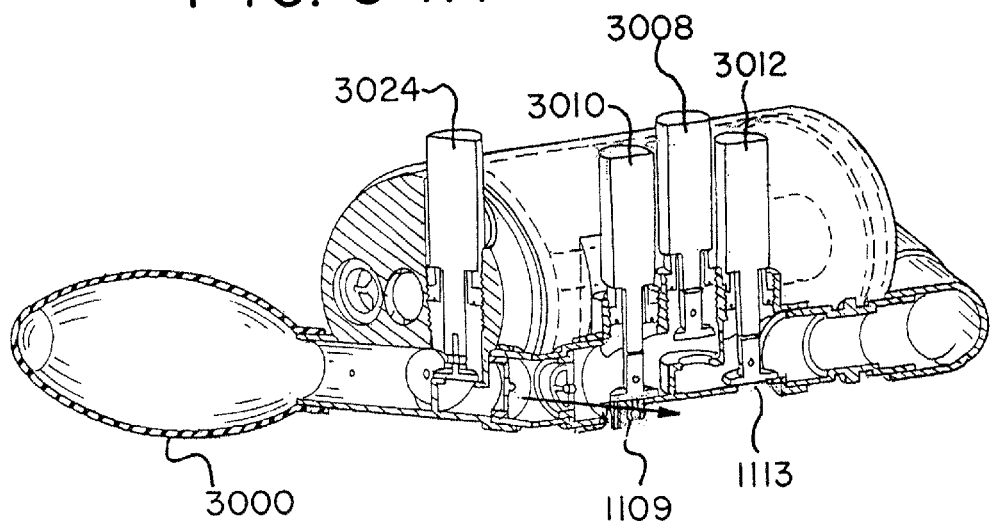
Figure 54B:
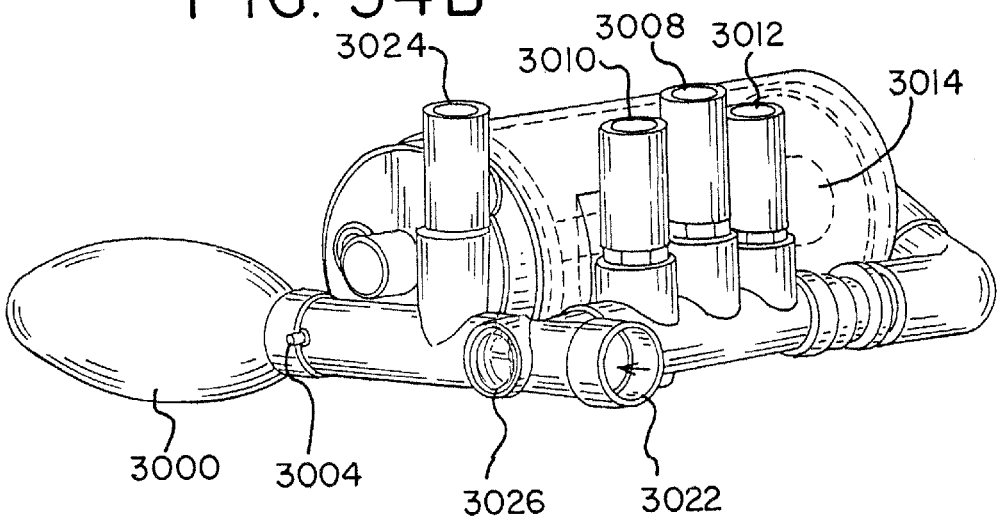

Initially, and referring to FIGS. 47 and 48, the inhalation membrane 3000 is primed through a priming port 3004 to get the membrane above its opening volume. This priming is currently performed with a hand pump. The system is then turned on. Referring to FIG. 49, valve 3008 is the only valve in the open position, allowing the user's exhaled breath to flow from the interface 3002 through port 1111 and into the exhalation membrane 3014, causing it to expand. Referring to FIG. 50, as the exhalation membrane 3014 expands inside the exhalation chamber, the membrane 3014 drives the surrounding atmospheric air through a check valve 3016 and into the inhalation membrane 3000, causing the membrane 3000 to expand. Referring to FIG. 51, when the exhalation membrane 3014 expands to a certain pressure as sensed by pressure port 3018, valve 3008 closes and valves 3010 and 3012 open. Valve 3012 allows the air inside the exhalation membrane 3014 to escape out to atmosphere through outlet 1113. Valve 3010 allows the user to finish his/her exhalation through a high resistance port 1109 (continuing PEP therapy). As the exhalation membrane 3014 deflates, it draws fresh atmospheric air into the exhalation chamber through a separate check valve 3020. Referring to FIGS. 52 and 53, the user can continue to exhale even if the exhalation membrane 3014 is already emptied. Once the user's airway pressure drops to a desired PEEP value (positive end expiratory pressure) as determined by pressure port 3018, valves 3010, 3012 close and the inhalation valve 3024 opens. The inhalation valve 3024 is the only valve open and connects the user to the inhalation membrane 3000 through the interface 3002. Pressurized air is driven into the user's airways until the inhalation membrane 3000 reaches its closing pressure as determined by pressure port 3006. At this point, the inhalation valve 3024 closes to prevent membrane 3000 collapse as shown in FIG. 54A. FIGS. 54A and B show internal and external views, with the inhalation valve 3024 closing at the inhalation membrane's closing pressure to prevent complete membrane closure. The remainder of the user's inhalation is at atmospheric pressure through a check valve 3026 as shown in FIG. 54b. Pressure ports 3006, 3018 feed readings to a control circuit which also drives the solenoids. Opening and closing pressures can be adjusted by changing the variable values in the software. In addition, an exhalation resistance adjustment screw and a volume adjustment plate/screw may be provided to allow the user to adjust how much resistance they feel when they are exhaling through port 1109. The volume adjustment plate/screw allows the user to adjust the device so that it is tuned to their own exhaled volume.

Figure 42A:
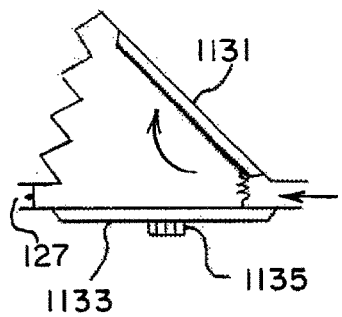
FIGS. 42A-C are schematic views showing a mechanism for emptying a chamber.
Figure 42B:
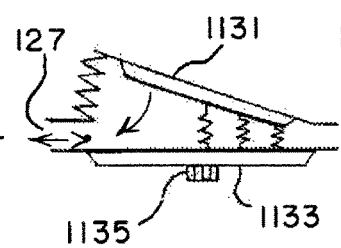
Figure 42C:
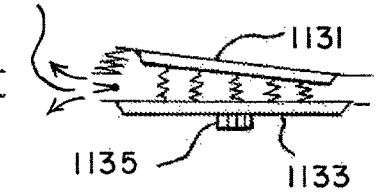

Referring to FIGS. 42A-C, an adjustable magnet 1135 is positioned underneath the element 102, which is provided with a metalized top 1131 and a "V" shape in cross-section. The top 1131 raises with the expiratory air flow, with the attractive force of the magnet 1135 decreasing and thus reducing the required pressure to inflate the element 102. The pressure curve matches the natural pressure curve of normal or forced exhalations. After the opening of the valve 127, the metalized top 1131 of the element 102 drops and the attractive force increases to squeeze the top against the base 1133, forcing the residual air to expel. Alternatively, an electro-magnetic force may be applied intermittently. In one embodiment, the attractive force may be applied only when the valve 127 is opened, thereby optimizing the efficiency of the system as no opening resistance would be opposed to the user's exhalation force, preserving this energy to inflate the inhalation reservoir 114. The mechanism of FIGS. 42A-C may be used in combination with the systems of FIGS. 39-41.

The following scenario provides an example of the interaction between the breathing assistance device with permissive hypercapnia and a user. In one exemplary embodiment, a hypothetical adult male has an anatomical dead space of 150 cc.

The following scenario has these parameters: Peak expiratory pressure: 20 cm H2O, PEEP: 5 cm H2O, and member 301 and 302 compliance: 30 cc/cm H2O.

Tidal volume 400 cc

First exhalation: 400 cc.

The first exhaled 300 cc will inflate members 301, 302 to a volume of 300 cc. Member 301 will be at a pressure of 20 cm H2O and member 302 will be at a pressure of 10 cmH2O.

Valve 303 opens and patient exhales through its last 100 cc with member 301 emptying.

Member 301 will empty down to the PEEP level of 5 cm H2O which corresponds to a residual volume of 150 cc.

First inhalation: 400 cc.

Patient starts to breathe in 15 cc of mixed air through the expiratory 304 and inspiratory 305 limbs, both pressurized to 5 cm H2O. As soon as the pressure drops to 4.5 cm H2O, valve 306, pre-adjusted to an opening pressure of 5 cm H2O opens to assist inhalation with fresh air pressurized to 10 cm H2O.

When the pressure reaches 4.5 cm H2O in member 302, 157.5 cc of fresh air and 7.5 cc of re-breathed air will have been provided to patient followed with 235 cc of mixed re-breathed air and fresh air coming from members 301, 302. Inhalation and exhalation membranes will have residual volumes of 17.5 cc each at the end of inhalation of 400 cc. The process repeats itself.

For recurrent CO2 inhalation, one has to choose a high ratio PEEP Peak Pressure to increase the inhaled CO2, e.g., 8/10 while a low ratio PEEP Peak pressure will lower CO2 inhalation, e.g., 4/10. Another means to vary the inhaled CO2 will be in choosing an asymmetrical compliance for members 301, 302, e.g., a ratio of 30 cc/cmH2O for member 301 versus a compliance of 15 cc/cmH2O for member 302, which will cause higher inhaled CO2 than a ratio of 15 cc/cmH2O for both members 301, 302. These variables give full control on the amount of permissive inhaled CO2.

Referring to FIGS. 37 and 38, the valve 229 previously discussed may be provided with a magnetic strip 333 coupled to an electromagnetic generator 334 instead of the regular magnetic strip 203 controlled with the adjustment device 209. A battery 335 or AC operated electromagnetic generator 334 is coupled to magnetic strips 333, a motion sensor 336, a chronometer 337 and a meter 338 (to monitor valve 229 openings pattern). When the number of openings/min falls under a pre-set rate, a command is sent to the generator 334 to increase the electromagnetic forces evenly applied to the magnetic bands 333 on valve 303 and valve 306, or other valves 229, so to gradually increase the required force to open these valves and therefore, the airways pressures.

On the other hand, when a stable breathing pattern is recognized through monitoring, a command is sent to the generator 334 to decrease the electromagnetic forces applied to the magnetic bands 333 so to gradually decrease the airways pressures. This electronic module 339 allows gradual increasing or decreasing positive airways pressures in order to meet the ever changing user's needs throughout a single night. For instance, a patient may benefit from very low pressures while falling asleep, which provides the advantages of a ramp and later on be confronted with much higher pressures, as OSA come up while deeply sleeping.

Referring to FIGS. 38A and B, one embodiment of a breathing assistance device provides a means to get over obstructed airways during potential episodes of obstructive sleep apnea. A compressor 349, used with the optional meter 338, directs the users to find the best parameters for any individual who wants to prevent OSA with the least amount of pressure. The compressor mechanism 349 includes: an electrical source 335, a small motor 341, a strap 342, a dome 343, a motion sensor 336, a chronometer 337 and an events meter 338.

After a pre-determined length of time without detecting patient's breathing, the compressor 349 squeezes the members 302, 347, 301 to generate a positive upper airways pressure to unblock the air passage and thus to allow some ventilation that help to maintain a decent blood oxygenation. Moreover, that little drive may be all a patient needs to change its breathing pattern and to resume a regular breathing with the breathing assistance device.

In operation, the motion sensor monitors the valve 303 openings. After a pre-determined number of seconds without valve 303 moving, a signal is sent to the small motor 341 that starts to turn its shaft 344, around which a strap 342 is wound into a bobbin 345. The strap 342 passes through guides 346 encircling the members 301, 302 and is fastened to a light plastic dome 343 covering 302. When the strap 342 pulls down on the dome 343, it squeezes Elements 302, 347 and 301, evacuating the volume of air contained in the breathing apparatus towards patient's airways as shown in FIG. 38B. The maximum pressure applied to the airways will be limited by the opening pressure of valve 303. An optional electromagnetic system 339 may be used with the valve 229 to gradually increase airways pressures as the patient falls asleep or if OSA resume. As soon as the valve 303 opens, a signal is sent to the small motor 341 that stops running. The shaft 344 then falls on neutral and the strap 342 starts to unroll, due to the member 347 memory recall and inflation of the member 302. The compressor 349 also may be supplied with AC current or via a 9 volt battery 335 for example. The breathing assistance device and compressor 349 may lie on a bedside table or be worn on patient's chest.

The optional events meter 338 is in line with the motion sensor 336 signal, and will count the number of times the motor 341 starts to run hence the number of events during a period of time. The meter 338 is resettable to 0. This information can be very useful to determine the most advantageous parameters setting (if the electromagnetic valve 229 is not used).

The compressor 349 provides many advantages over the existing CPAP machines, including no continuous airflow that dries up mucosa, no need for an expensive humidifier, decreased daily maintenance, very portable and autonomous, quiet operation, lower purchasing cost, and lower operational cost.

Referring to FIGS. 5A-F, 7 and 21, another embodiment of a breathing assistance apparatus includes a housing 400 having an exhalation chamber 402 and an inhalation chamber 404. The exhalation chamber is divided into two variable volume chambers 406, 408 sealingly separated by a displaceable piston 410, biased by a spring 412, and a rolling diaphragm 414 sealing the two variable chambers 406, 408 one from the other. The piston and diaphragm may be integrally or separately formed. The first variable chamber 406 holds an exhaust gas, while the other variable chamber 408 is connected to the inhalation chamber 404. Both variable chambers 406, 408 include inlet and outlet ports 416, 418, 420, 422. The inlet and outlet ports 420, 422 on the second variable chamber 408 are configured with one-way valves 424, 426. The spring 412 biases the piston 410 and valve 414 upwardly to minimize the volume of the first variable chamber 406.

The inhalation chamber 404 also includes a piston 428 and rolling diaphragm 430 separating two variable volume chambers 432, 434. Only the upper chamber 432 however, includes an inlet and outlet port 438, 440. A spring 436 biases the piston 428 and diaphragm 430 upwardly to minimize the volume of the upper, variable inhalation chamber 432. Again, the piston and diaphragm may be integrally or separately formed.

In operation, the user exhales, with the exhaled breath passing through the inlet port 416 of the exhaust gas chamber 402 and pushing the diaphragm 414 and piston 410 against the force of the spring 412 downwardly to descend in the exhalation chamber 402. This movement increases the pressure in the second variable chamber 408. The pressure opens the one-way valve 424, with air traveling through a conduit to the inhalation chamber 404 through the inlet port 438. The increased pressure in the inhalation chamber 404 pushes the piston 428 downwardly therein against the force of the spring 436, and thereby increases the pressure in the inhalation chamber 404, including the variable upper chamber 432.

Upon pressurization of the inhalation chamber 404, 432, a valve 450 (described in detail below) opens in the outlet port 418 and allows the user's exhaled breath to escape the upper variable exhalation chamber 406. As the pressure on the upper side of the piston 410 drops, the spring 412 returns the piston 410 to its normal, at-rest position. At the same time, the pressure on the back-side of the piston 410 drops, with the inlet valve 426 opening to allow fresh atmospheric air into the lower variable chamber 408 to equalize the pressure. The exhalation valve 450 has a closing pressure that is lower than its opening pressure in order to independently control PEEP. At the end of exhalation, the patient inhales from the inhalation chamber 404, 432 via a mouthpiece 500, described below, having a one-way valve 502 to receive the stored inhalation assist, or pressurized air in the inhalation chamber. A second one-way valve 504 in the mouthpiece prevents the user from rebreathing their own exhaled breath. The entire process is repeated with each breath.

Figure 6:
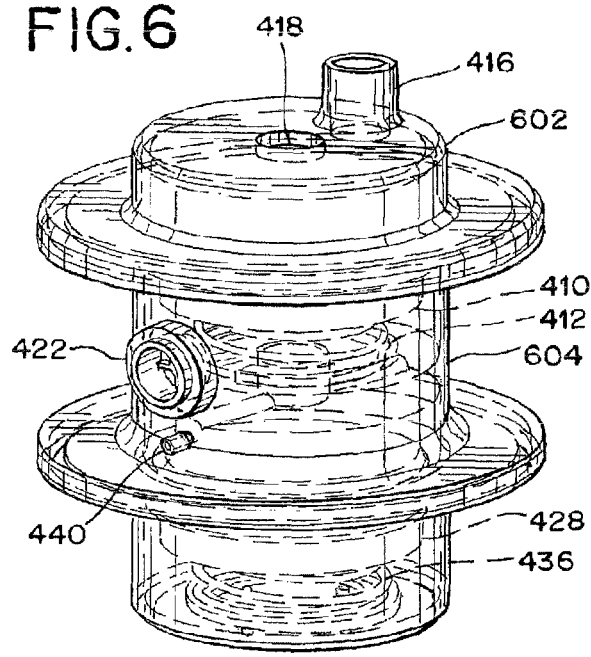
FIG. 6 is a perspective view of another embodiment of a breathing assistance apparatus.
Figure 7:
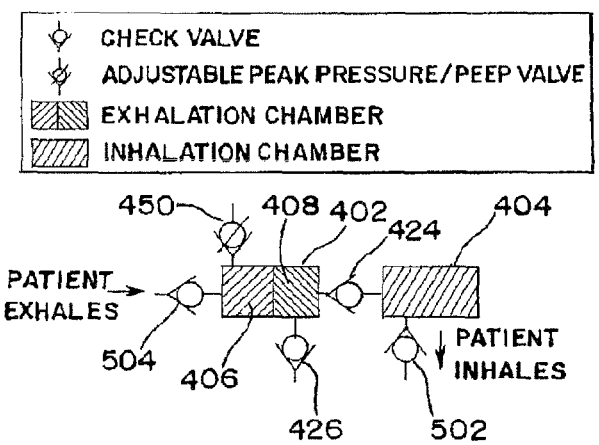
FIG. 7 is a schematic of a breathing assistance apparatus.
Figure 8A:
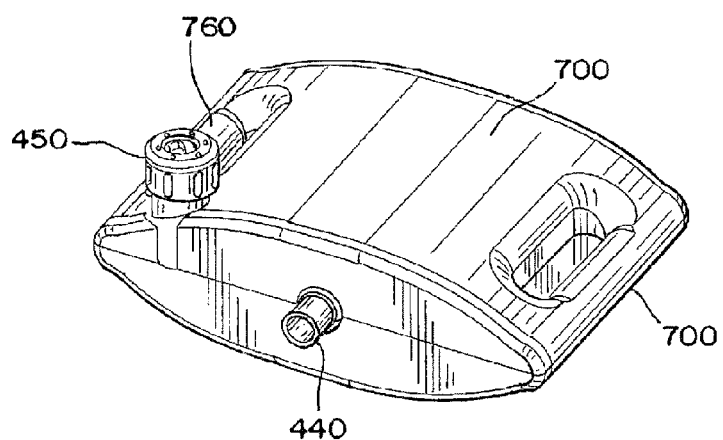
FIGS. 8A and B show top and bottom perspective view of another embodiment of a breathing assistance apparatus.
Figure 8B:
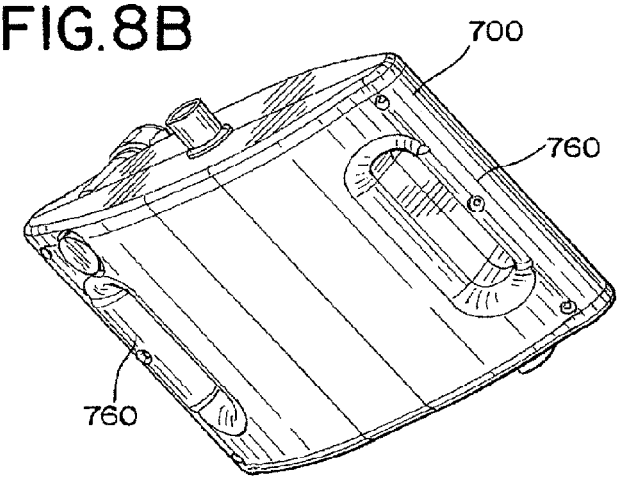

Referring to FIG. 6, an alternative embodiment of a breathing assistance apparatus is shown, but with the rolling diaphragm/valves arranged serially in chambers 602, 604 order to reduce the size of the device. The device operates in the same way as the embodiment of FIGS. 5A-F.

Referring to FIGS. 8A-10C and 24, an alternative embodiment of a breathing apparatus is shown as including a housing 700 with a pair of handles 760 disposed on opposite sides thereof. The housing has a clam-shell shape, and upper and lower components 702, 704 that are coupled together to form an interior cavity, which holds an exhalation and inhalation chamber 402, 404 and the coupling therebetween.

In one embodiment, the exhalation and inhalation chambers 402, 404 are each divided by elastic membranes 620, 622 rather than by pistons and springs. A first elastic membrane 620 is located inside an exhalation chamber, such that during inflation the membrane forces air into the inhalation chamber as explained above with respect to the spring and piston embodiment. The membrane 622, surrounded by air at atmospheric pressure, and alternatively the piston 410 and spring 412, are referred to as biasing members. One-way valves 424, 426 are arranged in the inlet and outlet ports as described above. The average exhalation chamber membrane 620 compliance, 100-150 cc/cmH2O, is relatively large compared to the inhalation chamber membrane 622, while having enough resilience to deflate completely within 1-2 seconds. For example, in one embodiment, an anesthesia bag may serve as the exhalation membrane 620.

The volume output of the device is dependent on several variables, including tidal volume, exhalation chamber and membrane volumes, inhalation chamber volume, inhalation and/or exhalation membrane compliance, number of exhalations before obtaining an inhalation assist, peak PEP setting, PEEP and dead space. Many of these variables may be adjustable. For example, as shown in FIGS. 10A-C, the exhalation chamber 630 may have a variable volume, and may be configured in one embodiment as an adjustable bellow. The exhalation membrane 620 is located inside the variable volume exhalation chamber 630, which is adjustable via a screw mechanism. A smaller volume exhalation chamber, e.g., a compressed bellow shown in FIG. 10A, would be more appropriate for users with lower tidal volumes, while a larger volume exhalation chamber, e.g., an expanded bellow shown in FIG. 10C, would be more appropriate for users with higher tidal volumes. The inhalation chamber membrane 622 may also be located in a variable volume housing, such as a bellow, which allows free expansion of the inhalation chamber, but which would allow the user to compress the bellow and thereby provided additional IPAP during inhalation.

The use of an elastic membrane 622 may provide certain advantages as shown in the graph at FIG. 11. Once opened, as the inhalation membrane 622 continues to expand, the internal pressure at any given time will decrease up to a certain volume. This means that for a user obtaining in inhalation assist from an elastic membrane, the pressure will remain at a near constant lever 1 during deflation for most of the volume delivered, whereas in the spring and piston embodiment of FIGS. 5A-F, the pressure will drop off linearly with volume. In this way, the elastic membrane provides a plateau-like pressure behavior.

The minimum peak pressure required to operate the elastic membrane embodiment is about 25 cmH$_2$O. Peak pressures lower than this amount may result in the membrane not opening. The exhalation membrane 620 with maximum compliance is desirable, such that minimal energy is expended in inflating the membrane, and will further reduce the peak pressure required to operate the device. Alternatively, a piston 632 of relatively large area may be exposed to the exhalation pressure and be coupled by way of a rod 636 or other link to a smaller piston 634 that pressurizes the inhalation chamber 402, 622 as shown in FIG. 25.

When using a high compliance exhalation membrane 622, a valve system may be necessary to ensure that the membrane deflates completely prior to subsequent exhalations.

Referring to FIGS. 12A-C, the mouthpiece 500 is shown as including a patient interface port 510, configured in one embodiment as a tube that is received in the user's mouth. The mouthpiece includes three flow paths 512, 514, 516 communicating with the interface port, with one-way valves 504, 502, 506 disposed in each flow path. A first flow path 512 communicates with the exhalation chamber inlet port 416 and a second flow path 514 communicates with the inhalation chamber outlet port 440. The third port 516 communicates with the atmosphere, such that the user may inhale freely through a one-way valve 506 once the inhalation chamber 404, 622 has emptied during the first third of inhalation. In an alternative embodiment of the mouthpiece, shown in FIG. 13, an additional user activated valve 520, such as a bite-valve, communicates with the inhalation port 514. In this way, the user may control when they want an inhalation assist, which is provided only when the valve 520 is activated by the user independent of their breathing. This may allow for a build-up of larger volume inhalation assists over the course of multiple exhalations. Alternatively, the interface 510 may be configured as a mask or a nasal insert.

Figures 14A, 14B:
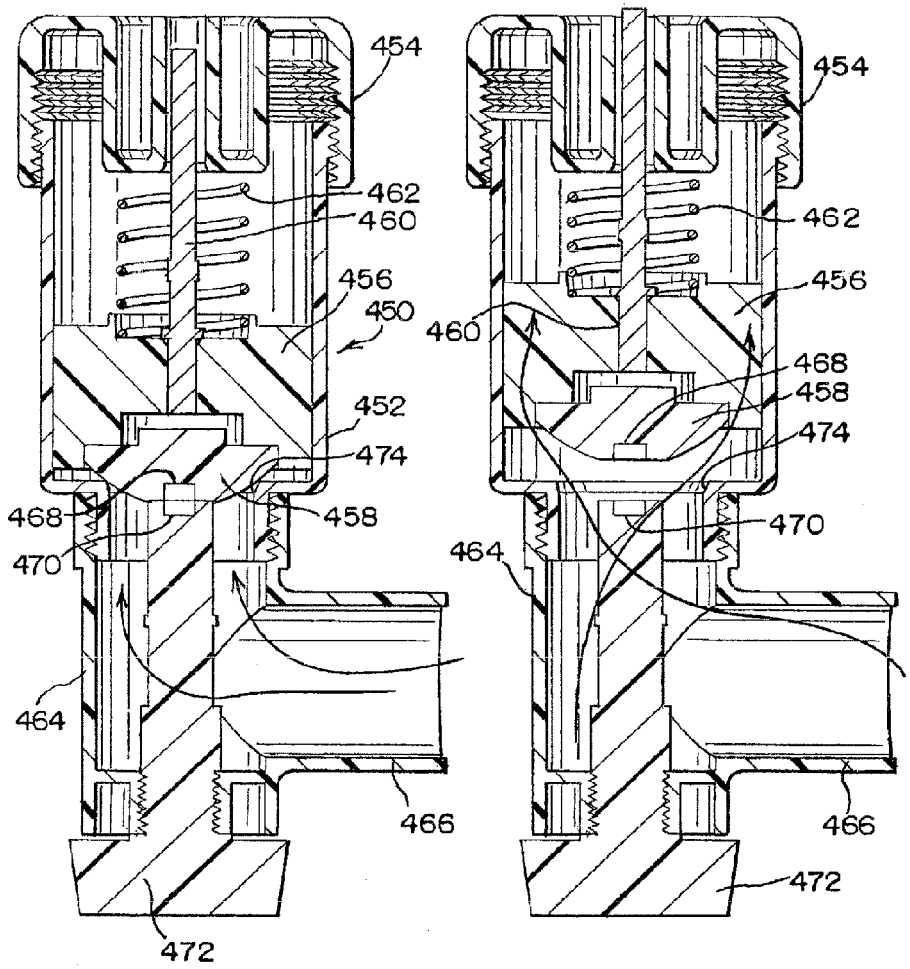
FIGS. 14A-B show the operation of one embodiment of a peak pressure and peep valve for use in the breathing assistance apparatus.
Figure 16A:
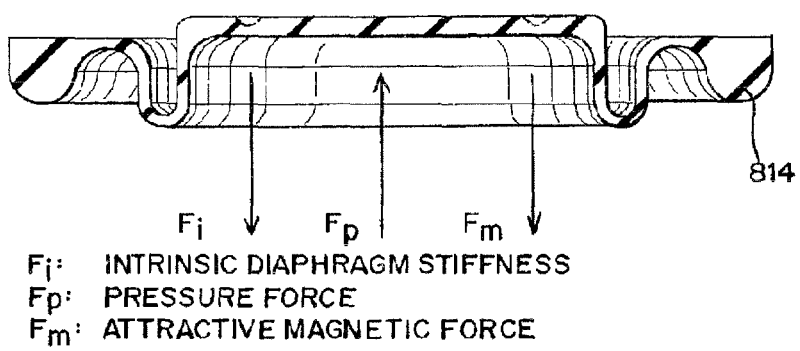
FIGS. 16A-B show a diaphragm used in the valve of FIGS. 15A and B.
Figure 16B:
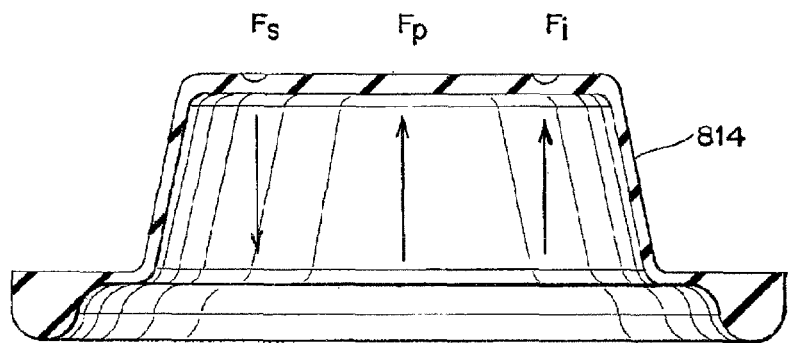

Referring to FIGS. 14A and B and 23, a peak pressure and peep valve 450 is shown. The valve opens at a set pressure, and re-seals or closes at a different, lower pressure. The opening and closing pressures are controlled and adjusted independently relative to each other. The valve 450 includes a piston housing 452 and spring adjuster member 454 threadably engaged with the piston housing. A piston 456 is disposed in the housing, and includes a sealing cone 458 at the bottom thereof. A spring guide 460 extends longitudinally within the housing, and a spring 462 is disposed between the adjuster member 454 and the piston 456. An adjuster housing 464 is coupled to the bottom of the piston housing, and includes a port 466 communicating with an interior thereof, and the bottom of the piston housing. In one embodiment, the sealing cone 458 is configured with a coupling member 468, such as a magnet. A peak pressure adjuster 472, configured with a rod with a second magnet 470, is threadably coupled to the adjuster housing 464. The adjuster 472 may be rotated such that the second magnet 470 is closer or further away from the sealing cone magnet 468, thereby applying a greater or lesser coupling force therebetween.

In a closed state, shown in FIG. 14A, pressure is allowed to build up on a upstream side of the sealing cone 458, made of silicone so as to minimize leakage. Once sufficient pressure is created from the exhalation chamber communicated through port 466 from outlet port 418, the coupling force of the magnets 468, 470 is overcome such the sealing cone 458 is moved away from its valve seat 474, thereby allowing the pressure to be applied to the piston 456. The opening pressure may be adjusted and controlled by varying the distance between the magnets 468, 470. As the pressure forces the piston 456 upward, the attractive force of the magnet drops off rapidly, and becomes negligible. At the same time, the spring 462 is compressed and provides resistance to the upward movement of the piston 456. The pressure is relieved by flow between the walls of the piston and the piston housing. Once the pressure drops below a certain threshold, the spring 462 pushes the piston 456 downwardly until the magnetic attractive force draws the sealing cone 458 closed against the valve seat 474. The closing pressure may be adjusted by adjusting the biasing force of the spring 462 by varying the position of the spring adjuster 454. In this way, the spring adjuster 454 is used to set the PEEP.

Referring to FIGS. 15A-16B and 20, an alternative peak pressure and peep valve 800 is shown. The valve opens at a set pressure, and re-seals or closes at a different, lower pressure. The opening and closing pressures are controlled and adjusted independently relative to each other. The valve includes a PEEP adjustment housing 802, a peak pressure housing 804, a PEEP adjuster 806 and a peak pressure adjuster 808. A PEEP piston 810 is disposed in the housing 802, with a spring 812 disposed between the piston 810 and adjuster 806. A popping diaphragm 814 is disposed adjacent the piston. A peak pressure piston 816 is disposed in the peak pressure housing. An adjustable coupling mechanism, configured as a pair of magnets 818, 820, is connected to the popping diaphragm 814.

Figure 17A:
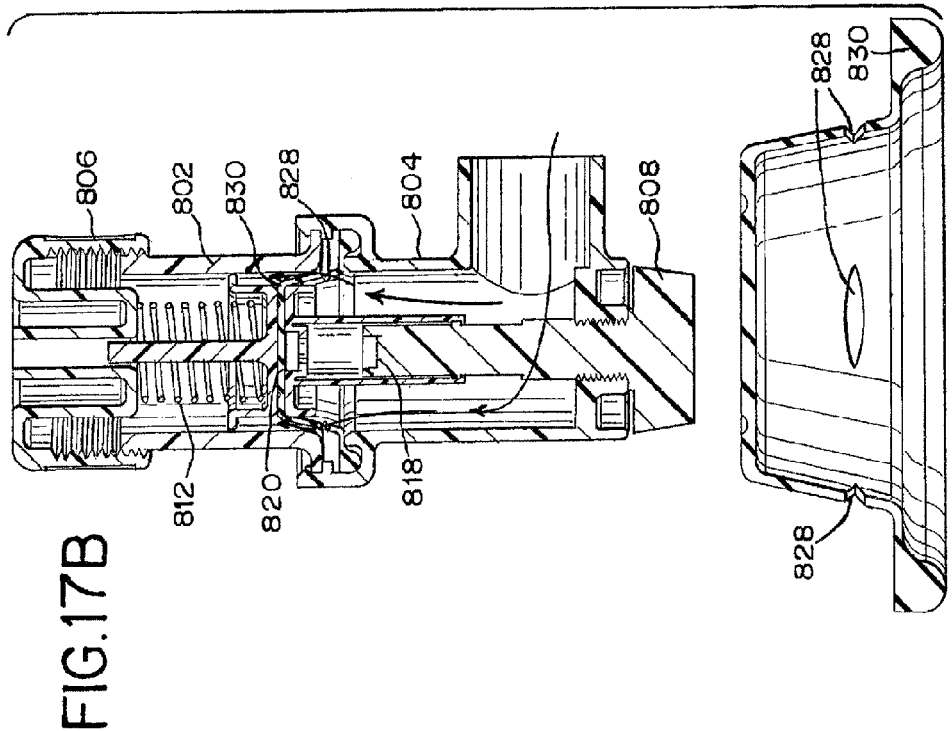
FIGS. 17A-B show an alternative embodiment of a peak pressure and peep valve.
Figure 17B:
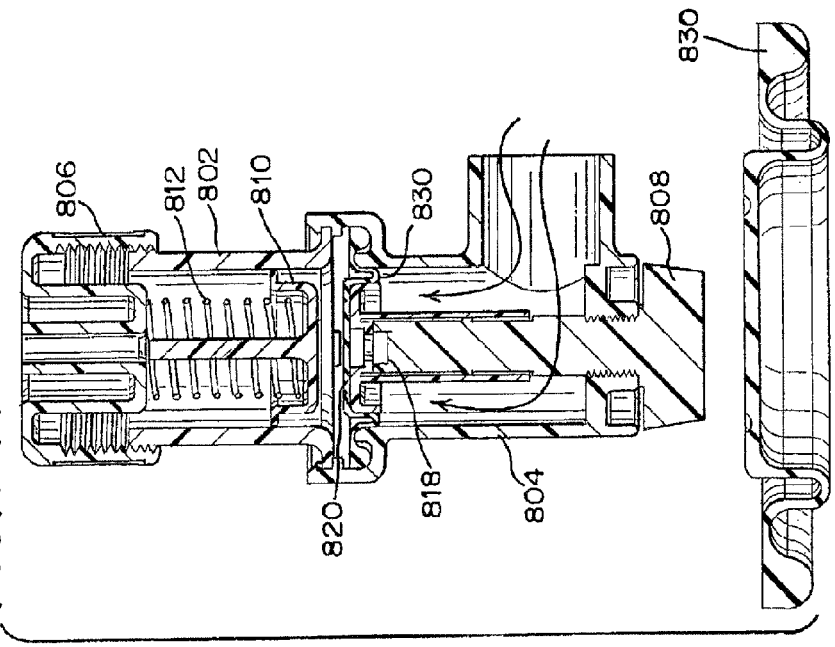
Figure 18A:
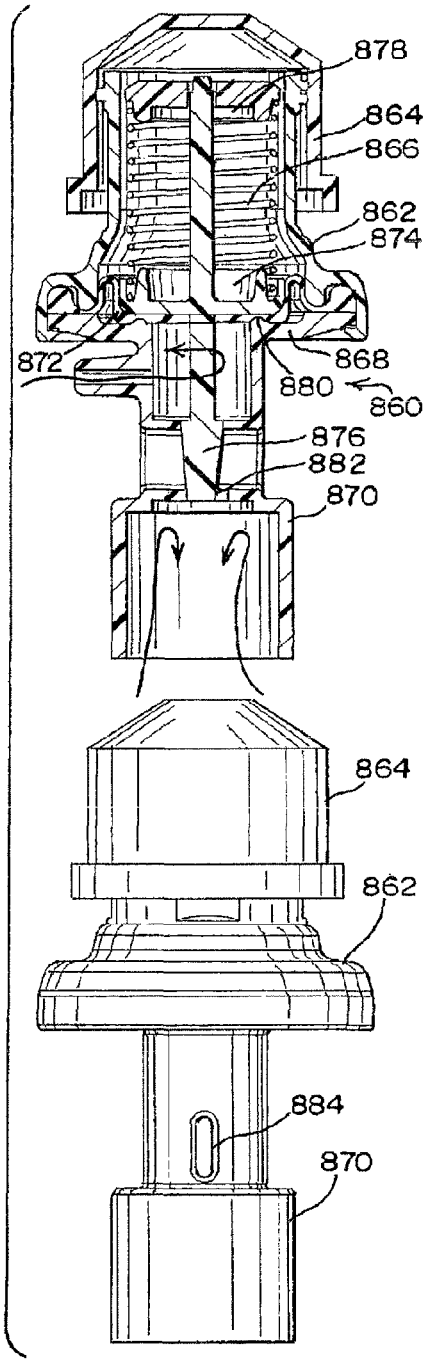
FIGS. 18A-B show an alternative embodiment of a peak pressure and peep valve.
Figure 18B:
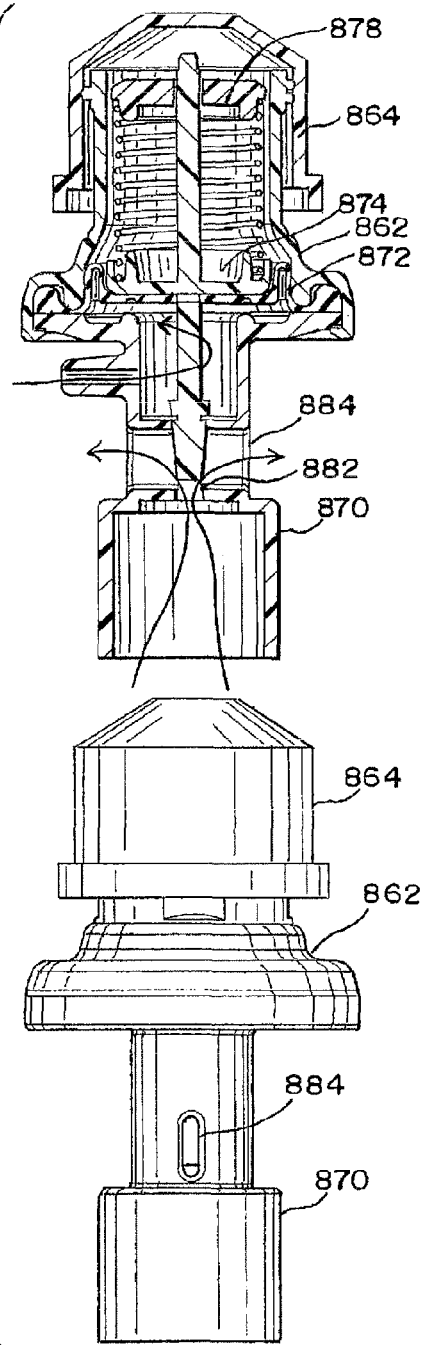
Figure 20:
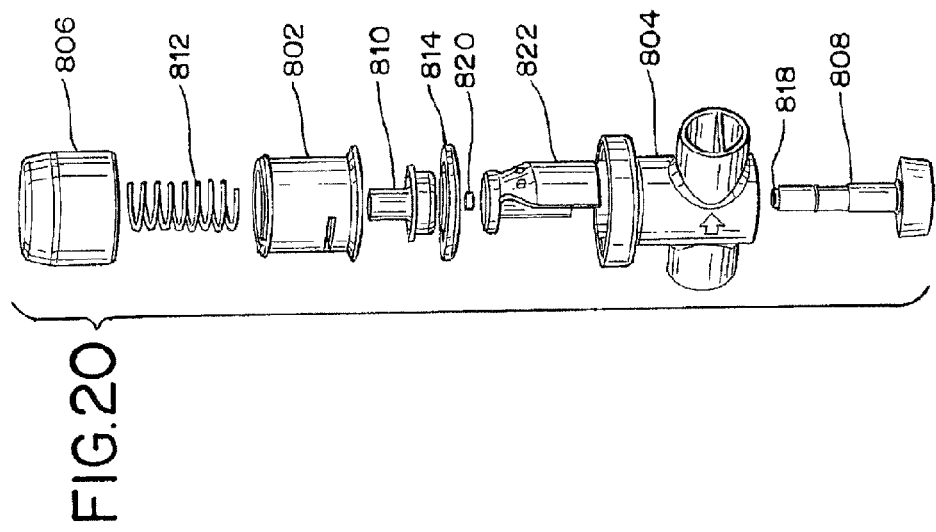
FIG. 20 is an exploded view of the valve shown in FIGS. 15A and B.
Figure 19A:
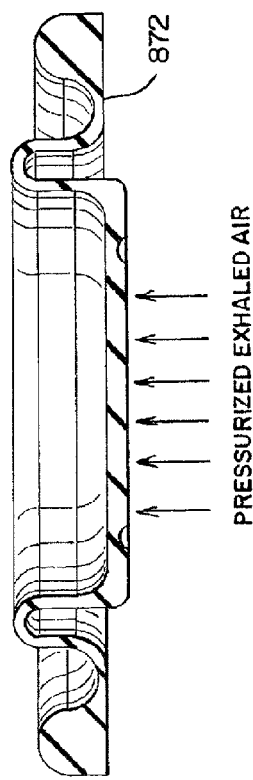
FIGS. 19A-B show a diaphragm used in the valve of FIGS. 18A and B.
Figure 19B:
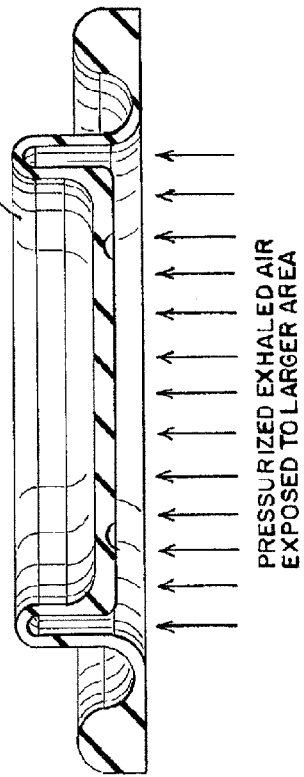
Figure 22:
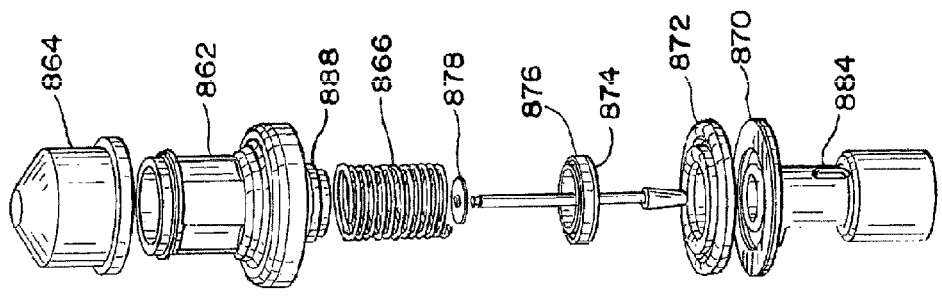
FIG. 22 is an exploded view of the valve shown in FIGS. 18A and B.
Figure 21:
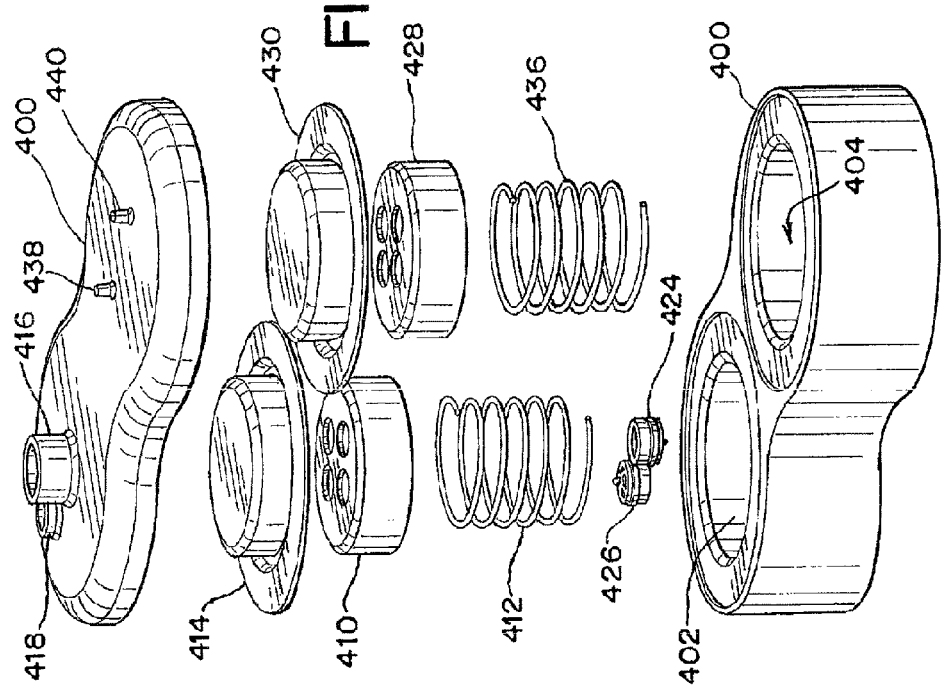
FIG. 21 is an exploded view of the breathing assistance apparatus shown in FIGS. 5A-F.

In a closed state, pressure is allowed to build on one side of the popping diaphragm 814. At a threshold pressure, the diaphragm 814 inverts due to an over-center geometry, pulling up a pressure release piston 816 having a gate 822. The gate 822 opens an exhalation passageway 824. The pressure required to open the gate may be adjusted, for example by varying the distance between the magnets 818, 820. The large travel experienced by the diaphragm 814 during the inversion process makes the attractive force negligible. The diaphragm 814 is stable in the inverted position due to the back pressure as it moves against the PEEP piston 810. The spring force exerted by the spring 812 against the PEEP piston 810 may be adjusted by adjusting the distance between the adjuster 806 and the piston 810. In this way, the pressure at which the diaphragm 814 will return to its initial state and close the gate 822 may be varied. In an alternative embodiment, shown in FIGS. 17A and B, slits 828 may be provided in the sides of the diaphragm 830 such that when the diaphragm is in an initial, non-inverted state, an airtight seal is created, but once inverted, air is able to pass through the slits 828 with some resistance, which would eliminate the need for the gate mechanism.

In another embodiment, shown in FIGS. 18A-19B and 22, an alternative peak pressure and peep valve 860 is shown. The valve 860 opens at a set pressure, and re-seals or closes at a different, lower pressure. The valve includes a spring housing 862, a spring adjuster 864, a spring 866, a spring retainer cap 868, a needle housing 870, a rolling diaphragm 872, a piston 874 with a sealing needle 876 and an isolating membrane 878. In a closed state, a small area of the rolling diaphragm 872 is exposed to pressurized exhaust air. A spring 866 applies a compression force to balance the pressurized force on the diaphragm 872. The spring force may be adjusted by a spring adjuster 864. Once an opening pressure is reached, the rolling diaphragm 872 translates upward, lifting off a sealing seat 880 and moving the sealing needle 876 from its seat 882. The lifting of the sealing needle 876 allows the pressurized air to escape from exposed outlet ports 884. At the same time, the rolling diaphragm 872 exposes more of its surface area to the pressurized air once opened, such that a lower pressure is required to keep the diaphragm 872 in an opened position. The ratio of the exposed areas in the closed and open position is as follows:

$P_{closed}A_{closed}=P_{open}A_{open}$ $P_{closed}$=Peak Pressure $P_{open}$=PEEP PEEP/Peak Pressure=$A_{closed}/A_{open}$ The adjustment spring 866 affects both pressures simultaneously, and in this embodiment, peak pressure and PEEP are not independently adjustable.

Balloons and other elastic membranes typically expand in a highly non-linear fashion. Upon reaching a peak pressure, referred to herein as the opening pressure, the elastic membrane readily expands. As the elastic membrane expands, the elastic membrane's walls thin out as they are stretched, making it easier to expand the elastic membrane further until the elastic membrane is stretched or otherwise expanded to its limit. At this point, pressure begins to build and risk of rupture increases. This is known as the valley pressure point or local minimum pressure point. The average pressure between the opening pressure and the pressure at the local minimum pressure point is referred to herein as the plateau pressure.

In one or more of the embodiments disclosed herein, the opening pressure for the inhalation membrane may be between 5 cmH2O-20 cmH2O, or preferably between 10 cmH2O-20 cmH2O, or most preferably between 12 cmH2O-15 cmH2O, and the plateau pressure for the inhalation membrane may be between 1 cm2O-20 cmH2O, or preferably between 8 cmH2O-20 cmH2O, or most preferably between 8 cmH2O-12 cmH2O.

In one or more of the embodiments disclosed herein, the opening pressure for the exhalation membrane may be between 0.1 cmH2O-15 cmH2O, or preferably between 0.1 cmH2O-10 cmH2O, or most preferably between 0.1 cmH2O up to 5 cmH2O, and the plateau pressure for the exhalation membrane may be between 0.1 cmH2O and 10 cmH2O, or preferably between 0.1 cmH2O and 5 cmH2O or most preferably between 0.1 cmH2O and 2 cmH2O. The highest possible compliance is desired for the exhalation membrane as long as it has enough elasticity to deflate to its initial volume in a matter of a few seconds through a low resistance port.

In one or more of the embodiments disclosed herein, the volume for each of the inhalation membrane and the exhalation membrane at its local minimum pressure point may be between 300 cc-1000 cc, or preferably between 500 cc-1000 cc or most preferably between 500 cc-700 cc.

In one or more of the embodiments disclosed herein, the inhalation chamber comprises a biasing member such as a constant force spring to maintain the inhalation chamber at a constant pressure throughout the delivered volume.

The desired magnitude of the force of the constant force spring may be derived based on the product of the piston/rolling diaphragm cross-sectional area and the desired inspiratory positive airway pressure (IPAP)–$F_{spring}=A_{piston}P_{IPAP}$. In one or more of the embodiments, the inhalation chamber comprises a constant force spring having a force large enough to provide IPAP of 5 cmH2O to 20 cmH2O, or preferably between 8 cmH2O and 20 cmH2O, or most preferably between 8 cmH2O and 12 cmH2O.

In one or more of the embodiments disclosed herein, the exhalation membrane comprises a biasing member such as a constant force spring with just enough biasing force to return the piston/rolling diaphragm to its initial position at a pressure difference of the desired PEEP. In some embodiments, the force may be adjusted.

Another embodiment of the breathing apparatus comprises an exhalation member that is expandable and contractible, wherein said exhalation member comprises an inlet port adapted for fluid communication with a user interface and an outlet port; and an inhalation member that is expandable and contractible comprising an inlet port in fluid communication with said exhalation member and an outlet port in fluid communication with said user interface; wherein said exhalation member is expandable from a first volume to a second volume in response to an exhaust flow;

and wherein said inhalation member is expandable from a first volume to a second volume in response to a pressurized flow from said exhalation member to said inlet port of said inhalation member. The exhalation member or the inhalation member or both may comprise an elastic material. The exhalation member or the inhalation member or both may comprise(s) a biasing member.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A breathing apparatus comprising:
   an inhalation chamber having a port;
   an exhalation chamber having an inlet port and an outlet port, said outlet port in fluid communication with said port of said inhalation chamber through a first passageway;
   an interface in fluid communication with said port through a second passageway, and said interface in fluid communication with said inlet port through a third passageway;
   a first valve moveable between open and closed positions, said first valve positioned in said third passageway, wherein said third passageway is open between said interface and said inlet port when said first valve is in said open position, and wherein said third passageway is closed between said interface and said inlet port when said first valve is in said closed position;
   a second valve moveable between open and closed positions and positioned in said third passageway between said first valve and said interface, wherein said interface is in fluid communication with a first outlet in said third passageway when said second valve is in said open position;
   a third valve moveable between open and closed positions and positioned in said third passageway between said first valve and said inlet port of said exhalation chamber, wherein said exhalation chamber is in fluid communication with a second outlet in said third passageway when said third valve is in said open position; and
   a fourth valve moveable between open and closed positions and positioned in said second passageway, wherein said second passageway is open between said port and said interface when said fourth valve is in said open position, and wherein said second passageway is closed between said port and said interface when said fourth valve is in said closed position.

2. The breathing apparatus of claim 1 wherein said first and second valves are configured such that said second valve is in said open position when said first valve is in said closed position, and said second valve is in said closed position when said first valve is in said open position.

3. The breathing apparatus of claim 2 wherein said first and third valves are configured such that said third valve is in said open position when said first valve is in said closed position, and said third valve is in said closed position when said first valve is in said open position.

4. The breathing apparatus of claim 3 wherein said second and third valves are configured such that said second and third valves are simultaneously moveable between said open and closed positions.

5. The breathing apparatus of claim 1 wherein said second valve is configured such that said second valve does not close said third passageway when said second valve is in said closed position.

6. The breathing apparatus of claim 1 wherein said third valve is configured such that said third valve does not close said third passageway when said third valve is in said closed position.

7. The breathing apparatus of claim 1 wherein said first outlet comprises a high resistance port.

8. The breathing apparatus of claim 1 further comprising a first check valve in communication with said exhalation chamber, said first check valve moveable between a closed position to an open position to permit air flow into said exhalation chamber.

9. The breathing apparatus of claim 8 wherein said first check valve and said second and third valves are configured such that said first check valve is moveable to said open position when said second and third valves are in said open positions.

10. The breathing apparatus of claim 8 further comprising a second check valve disposed in said first passageway, said second check valve moveable between a closed position to an open position to permit air flow out of said exhalation chamber and into said inhalation chamber through said first passageway.

11. The breathing apparatus of claim 10 wherein said first valve and said second check valve are configured such that said second check valve is moveable to said open position when said first valve is in said open position.

12. The breathing apparatus of claim 1 wherein said first, second, third and fourth valves are configured such that said fourth valve is moveable to said open position when said first, second and third valves are moveable to said closed position.

13. The breathing apparatus of claim 1 further comprising a first pressure port in communication with said second passageway.

14. The breathing apparatus of claim 13 further comprising a second pressure port in communication with said third passageway.

15. The breathing apparatus of claim 14 wherein said first, second, third and fourth valves comprise solenoid valves, and wherein said first, second, third and fourth valves are moveable in response to predetermined pressures at said first and second pressure ports.

16. The breathing apparatus of claim 1 further comprising a priming port in fluid communication with said inhalation chamber.

17. The breathing apparatus of claim 1 wherein said inhalation chamber comprises an expandable inhalation membrane.

18. The breathing apparatus of claim 1 wherein said exhalation chamber comprises a housing and an expandable exhalation membrane disposed in said housing, said housing and said exhalation membrane defining separate variable first and second volumes respectively, wherein said second volume of said exhalation membrane is in fluid communication with one of said inlet and outlet ports, and wherein said first volume of housing is in fluid communication with the other of said inlet and outlet ports.

19. The breathing apparatus of claim 1 wherein portions of said first and second passageways overlap.

20. A method of assisting the breathing of a user comprising:
    exhausting air from an exhalation chamber to an inhalation chamber through a first passageway;

passing said air from said inhalation chamber to an interface through a second passageway and inhaling said air through said interface;

exhaling through said interface and thereby passing exhalation gas to said exhalation chamber through a third passageway;

closing a first valve and thereby closing said third passageway;

opening a second valve in said third passageway between said first valve and said interface and passing said exhalation gas from said interface to a first outlet; and opening a third valve in said third passageway between said first valve and said inlet port of said exhalation chamber and passing said exhalation gas from said exhalation chamber to a second outlet.

21. The method of claim 20 wherein said passing said air from said inhalation chamber to said interface comprises opening a fourth valve in said second passageway.

22. The method of claim 21 wherein said opening of said first valve and said closing of said second and third valves occur simultaneously.

23. The method of claim 20 further comprising opening a first check valve in said exhalation chamber and passing fresh air into said exhalation chamber through said first check valve.

24. The method of claim 23 wherein said exhausting said air from said exhalation chamber to said inhalation chamber further comprises opening a second check valve disposed in said first passageway.

25. The method of claim 21 wherein said opening said fourth valve in said second passageway comprises determining a pressure with a pressure port in communication with said third passageway.

26. The method of claim 25 further comprising determining a second pressure with a second pressure port in communication with said second passageway and closing said fourth valve in said second passageway.

27. The method of claim 20 wherein said exhausting air from said exhalation chamber to said inhalation chamber comprises exhausting air from a first, variable volume defined by one of a housing or an exhalation membrane disposed in said housing, and wherein said passing exhalation gas to said exhalation chamber through said third passageway comprises passing said exhalation gas to a second, variable volume defined by the other of said exhalation membrane and said housing.

28. The method of claim 20 wherein portions of said first and second passageways overlap.

* * * * *